US010350148B2

(12) United States Patent
Enomura et al.

(10) Patent No.: US 10,350,148 B2
(45) Date of Patent: Jul. 16, 2019

(54) COMPOSITION FOR LAMINATED COATING FILM COMPRISING IRON OXIDE PARTICLES COATED WITH SILICON OXIDE

(71) Applicant: M. TECHNIQUE CO., LTD., Izumi-shi, Osaka (JP)

(72) Inventors: Masakazu Enomura, Izumi (JP); Daisuke Honda, Izumi (JP)

(73) Assignee: M. TECHNIQUE CO., LTD., Izumi-Shi, Osaka (JP)

(*) Notice: Subject to any disclaimer, the term of this patent is extended or adjusted under 35 U.S.C. 154(b) by 0 days.

(21) Appl. No.: 15/532,055

(22) PCT Filed: Oct. 5, 2016

(86) PCT No.: PCT/JP2016/079709
§ 371 (c)(1),
(2) Date: May 31, 2017

(87) PCT Pub. No.: WO2017/061519
PCT Pub. Date: Apr. 13, 2017

(65) Prior Publication Data
US 2017/0292028 A1    Oct. 12, 2017

(30) Foreign Application Priority Data

Oct. 5, 2015  (JP) .................. 2015-197556
Jun. 2, 2016  (JP) .................. 2016-111346
(Continued)

(51) Int. Cl.
C09D 201/00    (2006.01)
C01G 49/00     (2006.01)
(Continued)

(52) U.S. Cl.
CPC .............. *A61K 8/0245* (2013.01); *A61K 8/04* (2013.01); *A61K 8/19* (2013.01); *A61K 8/25* (2013.01);
(Continued)

(58) Field of Classification Search
CPC .......... C09D 1/00; C09D 5/32; C09D 7/1266; C09D 201/00; B05D 1/38; B05D 3/0254;
(Continued)

(56) References Cited

U.S. PATENT DOCUMENTS 4,487,869 A   12/1984 Panush
4,517,249 A    5/1985 Panush
(Continued)

FOREIGN PATENT DOCUMENTS

JP    59-75960 A     4/1984
JP    60-106866 A    6/1985
(Continued)

OTHER PUBLICATIONS

Sheng Liu, Gang Wu, Hong-Zheng Chen, Mang Wang, Preparation and characterization of Fe3O4/SiO2 particles for dual-particle electrophoretic display, Synthetic Metals 162 (2012) 89-94.© 2011 Elsevier B.V. All rights reserved.*
(Continued)

*Primary Examiner* — Bijan Ahvazi
(74) *Attorney, Agent, or Firm* — Birch, Stewart, Kolasch & Birch, LLP

(57) ABSTRACT

The object of the present invention is to provide a composition for a laminated coating film having designability to a coated body and weather resistance. The present invention provides a composition for a laminated coating film, comprising silicon oxide-coated iron oxide particles, wherein at least a part of the surface of said iron oxide particles is coated with silicon oxide, wherein the diameter of said iron
(Continued)

oxide particles is 1 to 50 nm, and wherein the average reflectivity of said silicon oxide-coated iron oxide particles for the light of the wavelengths of 620 to 750 nm is 25% or less. It is preferable that the transmittance of the dispersion comprising said silicon oxide-coated iron oxide particles for the light of the wavelength of 200 to 420 nm is 2.0% or less, and the transmittance of the same for the light of the wavelength of 620 to 780 nm is 80% or more.

10 Claims, 6 Drawing Sheets

(30) Foreign Application Priority Data

Jun. 3, 2016 (WO) .................. PCT/JP2016/066542
Jun. 22, 2016 (JP) ................................ 2016-123800

(51) Int. Cl.

| | |
|---|---|
| C01G 49/06 | (2006.01) |
| C09C 1/24 | (2006.01) |
| C09C 3/06 | (2006.01) |
| A61K 8/02 | (2006.01) |
| A61K 8/04 | (2006.01) |
| A61K 8/19 | (2006.01) |
| A61K 8/25 | (2006.01) |
| A61K 8/49 | (2006.01) |
| A61Q 1/02 | (2006.01) |
| A61Q 17/04 | (2006.01) |
| C09D 7/40 | (2018.01) |
| C09D 1/00 | (2006.01) |
| C09D 5/32 | (2006.01) |
| C01B 13/36 | (2006.01) |
| C01G 9/02 | (2006.01) |
| C09D 5/33 | (2006.01) |
| C08K 3/34 | (2006.01) |
| C09D 7/61 | (2018.01) |
| B82Y 30/00 | (2011.01) |
| C08K 3/22 | (2006.01) |

(52) U.S. Cl.
CPC .............. *A61K 8/4926* (2013.01); *A61Q 1/02* (2013.01); *A61Q 17/04* (2013.01); *C01B 13/36* (2013.01); *C01G 9/02* (2013.01); *C01G 49/06* (2013.01); *C08K 3/34* (2013.01); *C09D 1/00* (2013.01); *C09D 5/004* (2013.01); *C09D 5/32* (2013.01); *C09D 7/61* (2018.01); *C09D 7/67* (2018.01); *A61K 2800/413* (2013.01); *A61K 2800/43* (2013.01); *A61K 2800/621* (2013.01); *A61K 2800/651* (2013.01); *B82Y 30/00* (2013.01); *C01P 2002/72* (2013.01); *C01P 2002/82* (2013.01); *C01P 2004/04* (2013.01); *C01P 2004/32* (2013.01); *C01P 2004/64* (2013.01); *C01P 2004/84* (2013.01); *C08K 2003/2265* (2013.01)

(58) Field of Classification Search
CPC .......... B05D 5/063; B05D 5/066; B05D 7/14; C09C 1/24; C09C 3/06; C01G 49/00; C01G 49/06
USPC .................. 264/611; 310/216.066; 336/233; 427/380; 428/338; 977/811, 838
See application file for complete search history.

(56) References Cited

U.S. PATENT DOCUMENTS

| | | |
|---|---|---|
| 5,340,393 A | 8/1994 | Jacobson |
| 5,827,507 A | 10/1998 | Oshima et al. |
| 2002/0037262 A1 | 3/2002 | Tanaka et al. |
| 2002/0117084 A1 | 8/2002 | Hayashi et al. |
| 2002/0168523 A1 | 11/2002 | Uchida et al. |
| 2008/0134941 A1 | 6/2008 | Sanada |
| 2010/0155310 A1 | 6/2010 | Enomura |
| 2012/0130023 A1* | 5/2012 | Herzog .................. B82Y 30/00 525/386 |
| 2013/0342069 A1* | 12/2013 | Rowe ................ C04B 35/62807 310/216.066 |
| 2015/0030760 A1 | 1/2015 | Enomura |
| 2015/0152238 A1 | 6/2015 | Kobayashi |
| 2015/0202655 A1 | 7/2015 | Nakano et al. |
| 2015/0213927 A1* | 7/2015 | Katusic .................. C01G 49/00 427/127 |
| 2015/0217332 A1* | 8/2015 | Fujii ...................... B05D 5/068 427/380 |
| 2016/0104560 A1 | 4/2016 | Ohkoshi et al. |

FOREIGN PATENT DOCUMENTS

| | | |
|---|---|---|
| JP | 63-54979 A | 3/1988 |
| JP | 7-506081 A | 7/1995 |
| JP | 8-12961 A | 1/1996 |
| JP | 2000-2274 A | 1/2000 |
| JP | 2002-188021 A | 7/2002 |
| JP | 2002-308629 A | 10/2002 |
| JP | 2003-277644 A | 10/2003 |
| JP | 2006-249411 A | 9/2006 |
| JP | 2008-63200 A | 3/2008 |
| JP | 2008-239460 A | 10/2008 |
| JP | 2009-67613 A | 4/2009 |
| JP | 2009-112892 A | 5/2009 |
| JP | 2009-263547 A | 11/2009 |
| JP | 2013-249393 A | 12/2013 |
| JP | 2014-42891 A | 3/2014 |
| JP | 2014-42892 A | 3/2014 |
| WO | WO 98/26011 A1 | 6/1998 |
| WO | WO 2009/008393 A1 | 1/2009 |
| WO | WO 2013/128592 A1 | 9/2013 |
| WO | 2014/175387 A1 | 10/2014 |

OTHER PUBLICATIONS

Chao Hui, Chengmin Shen, Jifa Tian, Lihong Bao, Hao Ding, Chen Li, Yuan Tian, Xuezhao Shiab and Hong-Jun Gao, Core-shell Fe3O4@SiO2 nanoparticles synthesized with well-dispersed hydrophilic Fe3O4 seeds, Nanoscale, 2011, 3, 701-705.ᵃ The Royal Society of Chemistry 2011.*
Haowei Shi, Yan Huang, Chao Cheng, Guoyuan Ji, Yuxiang Yang, and Hongming Yuan, Preparation and Characterization of Chain-Like and Peanut-Like Fe3O4@SiO2 Core—Shell Structure, J. Nanosci. Nanotechnol. 2013, vol. 13, No. 10.*
Yang-Su Han, Seon-Mi Yoon, and Dong-Kuk Kim, Synthesis of Monodispersed and Spherical SiO2-coated Fe2O3 Nanoparticle, Bull. Korean Chem. Soc. 2000, vol. 21, No. 12 1193-1198.*
International Search Report for PCT/JP2016/066542 (PCT/ISA/210) dated Aug. 2, 2016.
International Search Report for PCT/JP2016/079709 (PCT/ISA/210) dated Nov. 29, 2016.
Written Opinion of the International Searching Authority for PCT/JP2016/079709 (PCT/ISA/237) dated Nov. 29, 2016.
Extended European Search Report, dated Mar. 21, 2019, for European Application No. 16853673.8.

* cited by examiner

COMPOSITION FOR LAMINATED COATING FILM COMPRISING IRON OXIDE PARTICLES COATED WITH SILICON OXIDE

TECHNICAL FIELD

The present invention relates to a composition for a laminated coating film comprising iron oxide particles coated with silicon oxide.

BACKGROUND ART

For a paint used to exterior walls and signboards in building materials, and vehicles and the like, not only color vividness and designability, but also light resistance against degradation by sunlight irradiation and durability against environmental change associated with weather changes are required. Thus, a substance that protects a coated body from ultraviolet rays and the like is used to protect components contained in a paint and a coating film, in a method of mixing it in the paint or in a method of coating it on the coating film.

Generally, use of a metal oxide as a material for protecting a coated body from ultraviolet rays and the like is effective for such paint. When the metal oxide is an iron oxide, it is required to reduce the influence of visible light, in order not to spoil protective ability from ultraviolet rays and the like for the coated body, as well as color characteristics such as a tint generated from the coated body, its chroma, transparency, and designability of a product. In particular, it is required that an iron oxide used in a red-colored paint transmits only red light, and absorbs visible lights other than red light as much as possible, for example, in case of identifying the color by lights passing through the coating film in a coated body.

As of an iron oxide for protecting a coated body from the ultraviolet rays and the like, Patent Literature 1 discloses a coloring pigment for sunlight high reflecting coating, comprising red iron oxide or yellow hydrous iron oxide having an average particle diameter of 10 nm to 300 nm. Patent Literature 2 discloses an iron oxide as a needle-shaped silica-coated Bengara red pigment having an average length of 500 nm and an average diameter of 100 nm. The iron oxide described in Patent Literature 1 or 2 may be used by mixing with the paint described in Patent Literature 3 or 4.

In a highly designed laminated coating film as described in Patent Literature 3 or Patent Literature 4 and a laminated coating film, by increasing difference between highlight (brightness, vividness) and shade (darkness) for a particular color when a light shines on a coated body, intensity of the reflected light varies greatly depending on the observation angle, to realize depth feeling, dense feeling and strong shadow sense (contrast of highlight and shade). Therefore, for a coating film comprising a coloring material such as an iron oxide, it is required to enhance transmittance for a particular color in order to enhance the highlight, and to reduce reflectivity for a particular color in order to increase difference between highlight and shade.

However, the iron oxide or the silica-coated iron oxide described in Patent Literature 1 and Patent Literature 2, have high average reflectivity in the visible region, especially in the range of the wavelength of 620 to 750 nm effective to a red-colored coated body. When used for the coating film or the coated body described in Patent Literatures 3 and 4, difference between highlight and shade is reduced, and the coating film or the coated body looks blurred, and especially color characteristics of a red paint or a red coating film, and designability of a coating film product are impaired. Thus, protection from ultraviolet rays and the like and transparency were incompatible. Further in the case of using the iron oxide particles in a paint and a coated body, the color characteristics of the iron oxide particles themselves are as important as those of the coloring material contained in the paint and the coated body. However, Patent Literature 2 describes the silica coating for inhibition of photocatalytic activity in the described silica-coated iron oxide, but does not describe specific silica coating for controlling color characteristics.

Further, Patent Literature 5 describes a black pigment of a solid solution of Cr and Fe. As shown in FIG. 2, the average reflectivity in the range of the wavelengths of 620 to 750 nm is 25% or less, but since the pigment is a black pigment, it is difficult to transmit lights in the visible region, in particular, lights in the wavelength of 620 to 750 nm exhibiting red color. Therefore, when the black pigment described in Patent Literature 5 is used particularly in a red paint, it is difficult to obtain high highlight, and designability of a coating film product is impaired. Further, in Patent Literature 5, the black pigment is manufactured by heat treatment at 800 to 1400° C., and in such condition particles usually tend to coarsen. The coating film using such particles tend to have lower transmittance and higher haze value, which may impair designability of a coating film product.

Patent Literature 6 filed by the present applicant discloses a method of producing various nanoparticles of an iron oxide and the like between two processing surfaces being capable of approaching to and separating from each other and rotating relative to each other. However, the iron oxide nanoparticles described in Patent Literature 6 are the nanoparticles of black iron oxide ($Fe_3O_4$: magnetite) and yellow iron oxide (FeOOH: goethite), and it was not observed that these iron oxide nanoparticles have ultraviolet ray protection ability, or properties to transmit or reflect a visible light, especially a red light. Further, in the first place, suppression of the specific characteristics expressing in oxide particles themselves was not described in Patent Literature 6, and thus, color characteristics of oxide particles themselves was not investigated sufficiently so far. Therefore, a composition for a laminated coating film is desired which can be suitably used in both aspects of ultraviolet ray protection ability and designability.

CITATION LIST

Patent Literature

Patent Literature 1: JP 2009-263547
Patent Literature 2: WO 1998/26011
Patent Literature 3: JP 2014-042891
Patent Literature 4: JP 2014-042892
Patent Literature 5: JP 2013-249393
Patent Literature 6: WO 2009/008393

SUMMARY OF THE INVENTION

Technical Problem

In light of such circumstances, an object of the present invention is to provide a composition for a laminated coating film, which does not spoil designability of a product, and is suitable for use in a laminated coating film. Particularly, an object of the present invention is to provide a composition for a laminated coating film, comprising silicon oxide-coated iron oxide particles, wherein at least a part of the surface of said iron oxide particles is coated with silicon oxide, wherein the diameter of said iron oxide particles is 1 to 50 nm, and wherein the average reflectivity of said silicon oxide-coated iron oxide particles for the light of the wavelengths of 620 to 750 nm is 25% or less, which is effective for a red-colored coated body.

Solution to the Problem

The present inventors have found that iron oxide particles wherein at least a part of the surface of the iron oxide particles is coated with silicon oxide, which color characteristics in the visible region is controlled, is applied to a composition for a laminated coating film. Then, the present inventors have accomplished the invention as follows.

Namely, the present invention provides a composition for a laminated coating film, comprising silicon oxide-coated iron oxide particles, wherein at least a part of the surface of said iron oxide particles is coated with silicon oxide, wherein the diameter of said iron oxide particles is 1 to 50 nm, and wherein the average reflectivity of said silicon oxide-coated iron oxide particles for the light of the wavelengths of 620 to 750 nm is 25% or less.

The present invention may be performed as a dispersion comprising said silicon oxide-coated iron oxide particles. It is preferred that the transmittance of said dispersion for the light of the wavelength of 200 to 420 nm is 2.0% or less, and the transmittance of the same for the light of the wavelength of 620 to 780 nm is 80% or more.

In the present invention, it is preferred that the haze value of said silicon oxide-coated iron oxide dispersion is 2.0% or less at the iron oxide concentration of 2 wt % in the dispersion comprising said silicon oxide-coated iron oxide particles.

The present invention may be performed wherein said silicon oxide comprises amorphous silicon oxide.

The present invention may be performed wherein said silicon oxide-coated iron oxide particles are the particles wherein at least a part of the surface of one iron oxide particle is coated with silicon oxide, and wherein the primary particle diameter of said iron oxide particle is 50 nm or less, and the primary particle diameter of said silicon oxide-coated iron oxide particles is 100.5% or more and 190% or less relative to said primary particle diameter of the iron oxide particle. The present invention may be performed wherein said silicon oxide-coated iron oxide particles are core-shell type silicon oxide-coated iron oxide particles wherein the entire surface of one core iron oxide particles is coated with the shell silicon oxide.

Further, the present invention may be performed wherein said silicon oxide-coated iron oxide particles are the particles wherein at least a part of the surface of the aggregates of a plurality of iron oxide particles is coated with silicon oxide, and wherein the diameter of said aggregates is 50 nm or less, and the diameter of said silicon oxide-coated iron oxide particles is 100.5% or more and 190% or less relative to the diameter of said aggregates.

The present invention may be performed as said composition for a laminated coating film comprising a perylene pigment.

Advantageous Effects of the Invention

The present invention enables to provide a composition for a laminated coating film, which has a high transparency, and does not impair performance of paints. In particular, the present invention enables to provide a composition for a laminated coating film, which does not impair designability of a product, and can be used efficiently for a coated body, by applying silicon oxide-coated iron oxide particles wherein at least a part of the surface of the iron oxide particles is coated with silicon oxide, and wherein the reflectivity in the visible region is controlled, to the composition for a laminated coating film.

DESCRIPTION OF THE INVENTION

Figure 1:
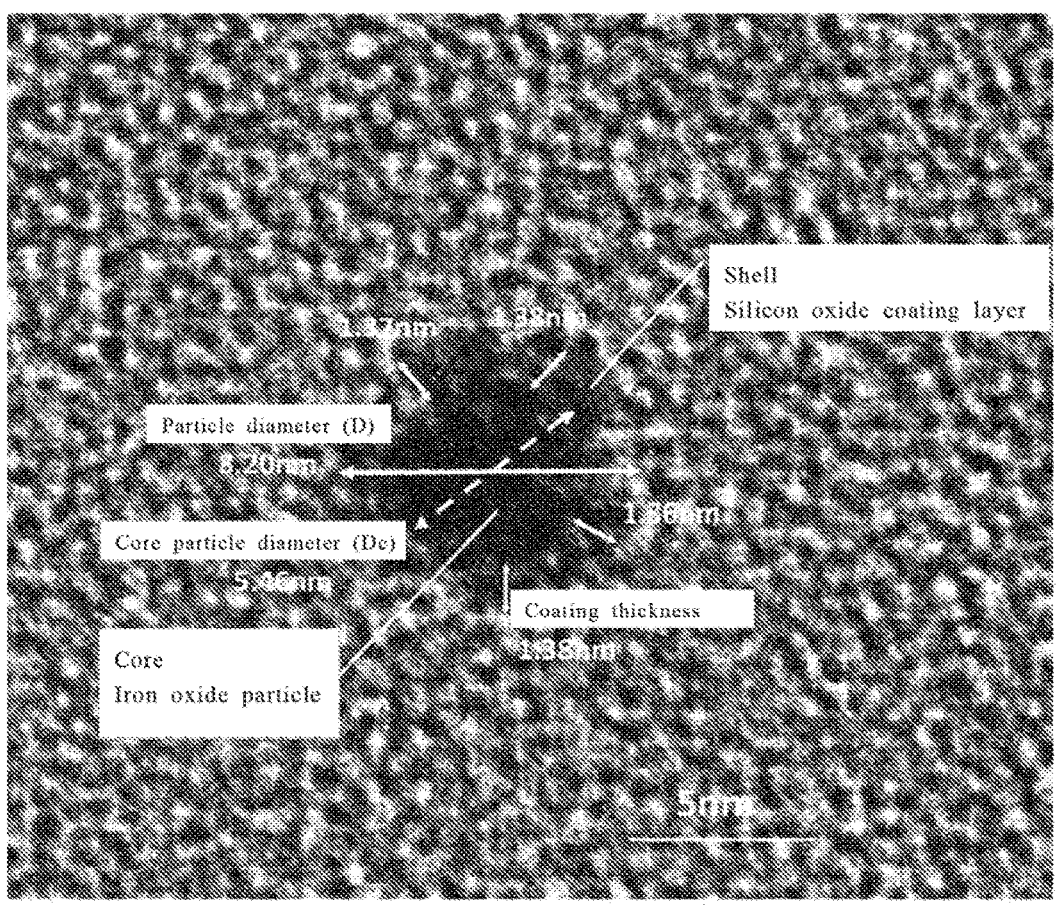
FIG. 1 shows a TEM photograph of the silicon oxide-coated iron oxide particles obtained in Example 1 of the present invention.

Hereinafter, the present invention is explained by embodiments of the present invention based on the drawings as an example. However, embodiments of the present invention are not limited only to the embodiments described hereinafter.

A composition for a laminated coating film of the present invention may be used suitably for application to a laminated coating film as described in Patent Literature 3 or 4, and has weather resistance. Weathering resistance is a generic term for light resistance against degradation by sunlight irradiation, durability against environmental changes associated with changes in weather, humidity and the like, and ability to protect a paint or a coated body from degradation of the components or the like contained in the coated body by photocatalytic activity and the like. However, when the conventional silicon oxide-coated iron oxide is applied to a paint to give weather resistance, color characteristics such as tint and chroma exhibited by the paint and transparency, and designability of a product may be impaired, and thus, a desired color characteristics may not be obtained. It was difficult to possess designability and weather resistance.

A composition for a laminated coating film of the present invention includes silicon oxide-coated iron oxide particles wherein at least a part of the surface of the iron oxide particles is coated with silicon oxide. Silicon oxide-coated iron oxide particles may be core-shell type silicon oxide-coated iron oxide particles wherein the entire surface of one core iron oxide particles is coated with shell silicon oxide. Further, the silicon oxide-coated iron oxide particles are preferably silicon oxide-coated iron oxide particles wherein a plurality of iron oxide particles are not aggregated, and at least a part of the surface of one iron oxide particle is coated with silicon oxide. But, the silicon oxide-coated iron oxide particles may be silicon oxide-coated iron oxide particles wherein at least a part of the surface of the aggregate wherein a plurality of iron oxide particles are aggregated, is coated with silicon oxide.

It is possible to use silicon oxide-coated iron oxide as a composition for coating or a pigment intended for a clear coating film for a red color painting, and to use silicon oxide-coated iron oxide suitably as a composition for a laminated coating film by mixing it with another pigment. Thus, silicon oxide coating at least part of the surface of iron oxide particles preferably comprises amorphous silicon oxide.

The iron oxide particles in the present invention should be interpreted to mean the particles composed of iron oxide as a main component. Even when particles include impurities mixed unintentionally or other components added intentionally, such particles are included in the iron oxide particles in the present invention as long as iron oxide is included in the particles more than other components in terms of a part by weight or a molar ratio.

A composition for a laminated coating film of the present invention, comprises powers of silicon oxide-coated iron oxide particles; a dispersion wherein silicon oxide-coated iron oxide particles are dispersed in a liquid dispersion medium; and a dispersion wherein silicon oxide-coated iron oxide particles are dispersed in a solid such as glass and resin, and the like. Silicon oxide-coated iron oxide particles included in the composition for a laminated coating film may be composed of silicon oxide-coated iron oxide particles wherein at least a part of the surface of one iron oxide particle is coated with silicon oxide, or may be composed of silicon oxide-coated iron oxide particles wherein at least a part of the surface of the aggregates of a plurality of iron oxide particles is coated with silicon oxide, or may be composed of both of those. Further, the composition for a laminated coating film may be used dispersed in a paint together with various pigments, or may be overcoated on a coating film. Further, the silicon oxide-coated iron oxide particles may be used as a sole pigment. A liquid dispersion medium includes water such as tap water, distilled water, RO water, pure water and ultrapure water; an alcohol solvent such as methanol, ethanol and isopropyl alcohol; a polyhydric alcohol solvent such as propylene glycol, ethylene glycol, diethylene glycol and glycerine; an ester solvent such as ethyl acetate and butyl acetate; an aromatic solvent such as benzene, toluene and xylene; a ketone solvent such as acetone and methyl ethyl ketone; a nitrile solvent such as acetonitrile, and the like. These dispersion media may be used alone or may be used by mixing a plurality of these dispersion media.

In the present invention, it is preferable that the diameter of the iron oxide particles is 1 to 50 nm. In case of silicon oxide-coated iron oxide particles wherein at least a part of the surface of one iron oxide particle is coated with silicon oxide, it is preferable that the primary particle diameter of the iron oxide particle is 1 to 50 nm. In case of silicon oxide-coated iron oxide particles wherein at least a part of the surface of the aggregate wherein a plurality of iron oxide particles are aggregated, is coated with silicon oxide, it is preferable that the diameter of the aggregate is 1 to 50 nm.

In the present invention, in case of silicon oxide-coated iron oxide particles wherein at least a part of the surface of one iron oxide particle is coated with silicon oxide, it is preferable that the primary particle diameter of the iron oxide particles is 1 to 50 nm, and it is preferable that the primary particle diameter of the silicon oxide-coated iron oxide particles is 100.5% or more and 190% or less relative to the primary particle diameter of the iron oxide particles. When silicon oxide coating is too thin relative to the iron oxide particles, the effect regarding the color characteristics of the silicon oxide-coated iron oxide particles and the effect to reduce photocatalytic ability may not exhibit. Thus, it is preferable that the primary particle diameter of the silicon oxide-coated iron oxide particles is not less than 100.5% relative to the primary particle diameter of the iron oxide particles. When the coating is too thick, or when coarse aggregates are coated, control of color characteristics is difficult. Thus, it is preferable that the primary particle diameter of the silicon oxide-coated iron oxide particles is not more than 190% relative to the primary particle diameter of the iron oxide particles.

Further, silicon oxide-coated iron oxide particles of the present invention may be silicon oxide-coated iron oxide particles wherein at least a part of the surface of the aggregates wherein a plurality of the iron oxide particles are aggregated, is coated with silicon oxide. However, a silicon oxide-coated iron oxide wherein aggregates exceeding a certain size are coated with silicon oxide is not preferable, since such silicon oxide-coated iron oxide particles may not have the effect of color characteristics such as reflectivity and the like, compared with silicon oxide-coated iron oxide particles wherein at least a part of the surface of one iron oxide particle is coated with silicon oxide. Here, the aggregate exceeding a certain size refers to those which magnitude is, for example, more than 50 nm. And, it is preferable that the particle diameter of the silicon oxide-coated iron oxide particles wherein at least a part of the surface of the aggregates wherein a plurality of the iron oxide particles are aggregated, is coated with silicon oxide, is 100.5% or more and 190% or less relative to the diameter of the aggregates, for the same reason as the silicon oxide-coated iron oxide particles wherein at least a part of the surface of one iron oxide particle is coated with silicon oxide. Here, a diameter of the aggregates refers to a maximum distance between two points on the outer periphery of the aggregates.

Figure 5:
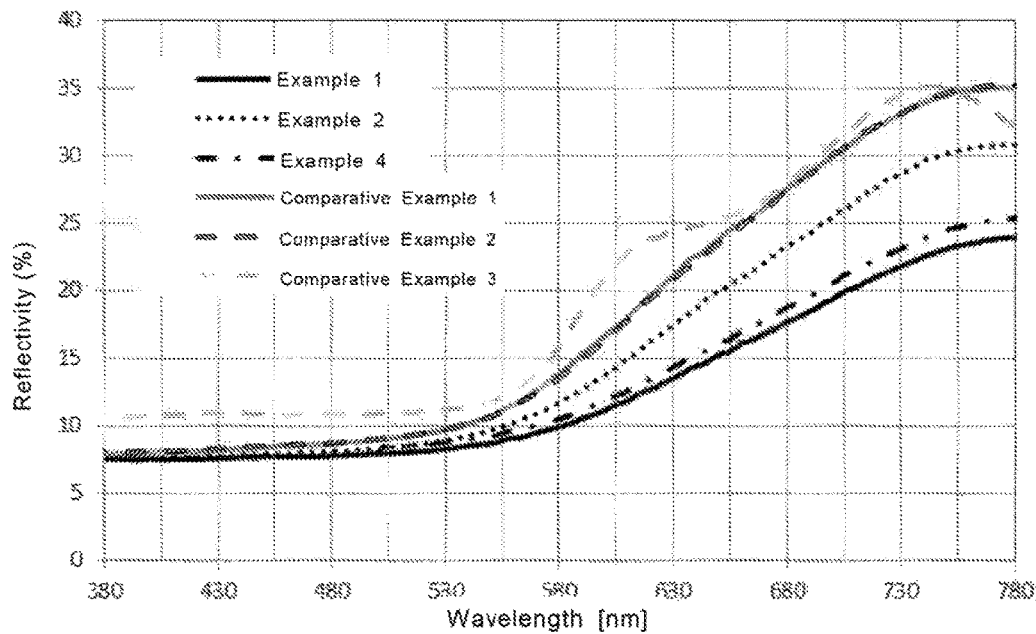
FIG. 5 shows the reflection spectrum measurement results of the silicon oxide-coated iron oxide particles obtained in Example 1, Example 2 and Example 4 of the present invention, and of the iron oxide particles obtained in Comparative Example 1, and of the silicon oxide-coated iron oxide particles obtained in Comparative Example 2, and of the iron oxide particles of Comparative Example 3 respectively.

FIG. 5 shows the reflection spectrum of the powders of silicon oxide-coated iron oxide particles of the present invention, specifically, of the powders of the silicon oxide-coated iron oxide particles obtained in Example 1, Example 2 and Example 4. By calculating average reflectivity for the light of the wavelengths of 620 to 750 nm from the reflection spectrum shown in FIG. 5, the average reflectivity of Example 1 is 18.1%, the average reflectivity of Example 2 is 23.7%, and the average reflectivity of Example 4 is 19.2%. The average reflectivities of Examples 1, 2 and 4 for the light of the wavelengths of 620 to 750 nm which are effective to a red-colored coated body, are 25% or less. Also, the average reflectivity of Example 3 is 20.2%, and the average reflectivity of Example 3 for the light of the wavelengths of 620 to 750 nm which are effective to a red-colored coated body, is 25% or less. When the average reflectivity for the light of the wavelengths of 620 to 750 nm exceeds 25%, difference between highlight and shade in the laminated coating film is reduced, and the properties of highlight and shade are impaired, and designability is reduced. Thus, in the present invention, the average reflectivity in the wavelength region of 620 to 750 nm is preferably 25% or less, and more preferably 20% or less.

Here, the average reflectivity for the light of the wavelengths of 620 to 750 nm refers to the simple average value of the reflectivity of each measurement wavelength in the wavelength region of the wavelengths of 620 to 750 nm.

When a composition for a laminated coated film comprising silicon oxide-coated iron oxide particles which average reflectivity for the light of the wavelengths of 620 to 750 nm is 25% or less, is applied to a paint, color characteristics exhibited by the paint is not impaired, and difference between highlight and shade in the laminated coated film may increase. Thus, a compound for a laminated coated film can be used in a laminated coated film suitably. A composition for a laminated coating film of the present invention may be used in a single-layer coating film.

The transmittance of the dispersion including silicon oxide-coated iron oxide particles (hereinafter, referred to as silicon oxide-coated iron oxide particle dispersion) of the invention for the light of the wavelengths from 200 nm to 420 nm is 2.0% or less, and the transmittance for the light of the wavelengths from 620 nm to 780 nm is 80% or more. The silicon oxide-coated iron oxide particle dispersion showing such transmittance absorbs an ultraviolet light and transmits a visible light. Iron oxide has a photocatalytic activity. In the state of not being coated with silicon oxide, iron oxide may absorb an ultraviolet ray, and exhibit photocatalytic activity to decompose various components such as a coloring material or a resin contained in a paint or a coated film, and dispersing agent and the like. But, by coating at least a part of the surface of iron oxide particles with silicon oxide, photocatalytic activity of iron oxide particles is suppressed.

The haze value of the dispersion wherein the silicon oxide-coated iron oxide particles obtained in Example 1 is dispersed in propylene glycol at a $Fe_2O_3$ concentration of 0.05 wt % is 0.00%. And, the haze value of the dispersion wherein the silicon oxide-coated iron oxide particles obtained in Example 1 is dispersed in water at a $Fe_2O_3$ concentration of 0.31 wt % is 0.08(0.00)%. Accordingly both dispersions are highly transparent dispersions. A haze value is a numerical value indicating transparency. For example, when a composition having a haze value exceeding 2% is applied on a paint of buildings or vehicles, a color of the paint as a foundation will be impaired, and thus the desired coloring will be inhibited. The present invention shows that a haze value of 2% or less of a dispersion at a $Fe_2O_3$ concentration of 2 wt % can be achieved. The haze value is more preferably 1.5% or less.

Such silicon oxide-coated iron oxide particle dispersion, or a paint, a coating film and a coated body prepared using the dispersion absorbs a light in the ultraviolet region, and further transmits a light in the visible region. Thus, the composition for a laminated coating film can protect and guard a coated body from an ultraviolet ray and the like without impairing bright color of a coloring material or transparency, as used for the purpose of blending it to a paint, or for the purpose of protecting a clear layer for painting.

In the present invention, it is considered to be a factor of completion of the present invention, that the transmittance of silicon oxide-coated iron oxide particles for the light of the wavelength of 200 to 420 nm is lower than that of conventional ones.

Factors for reduction of the transmittance of silicon oxide-coated iron oxide particles of the present invention for the light of the wavelength of 200 to 420 nm, are considered to be not only the increased surface area by the smaller particle diameter than that of conventional ones, but also higher crystallinity of the core iron oxide particles.

It have been found in the present invention that color characteristics, particularly reflectivity of silicon oxide-coated iron oxide particles and a composition for a laminated coating film can be controlled, by making silicon oxide in the silicon oxide-coated iron oxide particles used in the composition for a laminated coating film comprise amorphous silicon oxide, as shown below.

Figure 2:
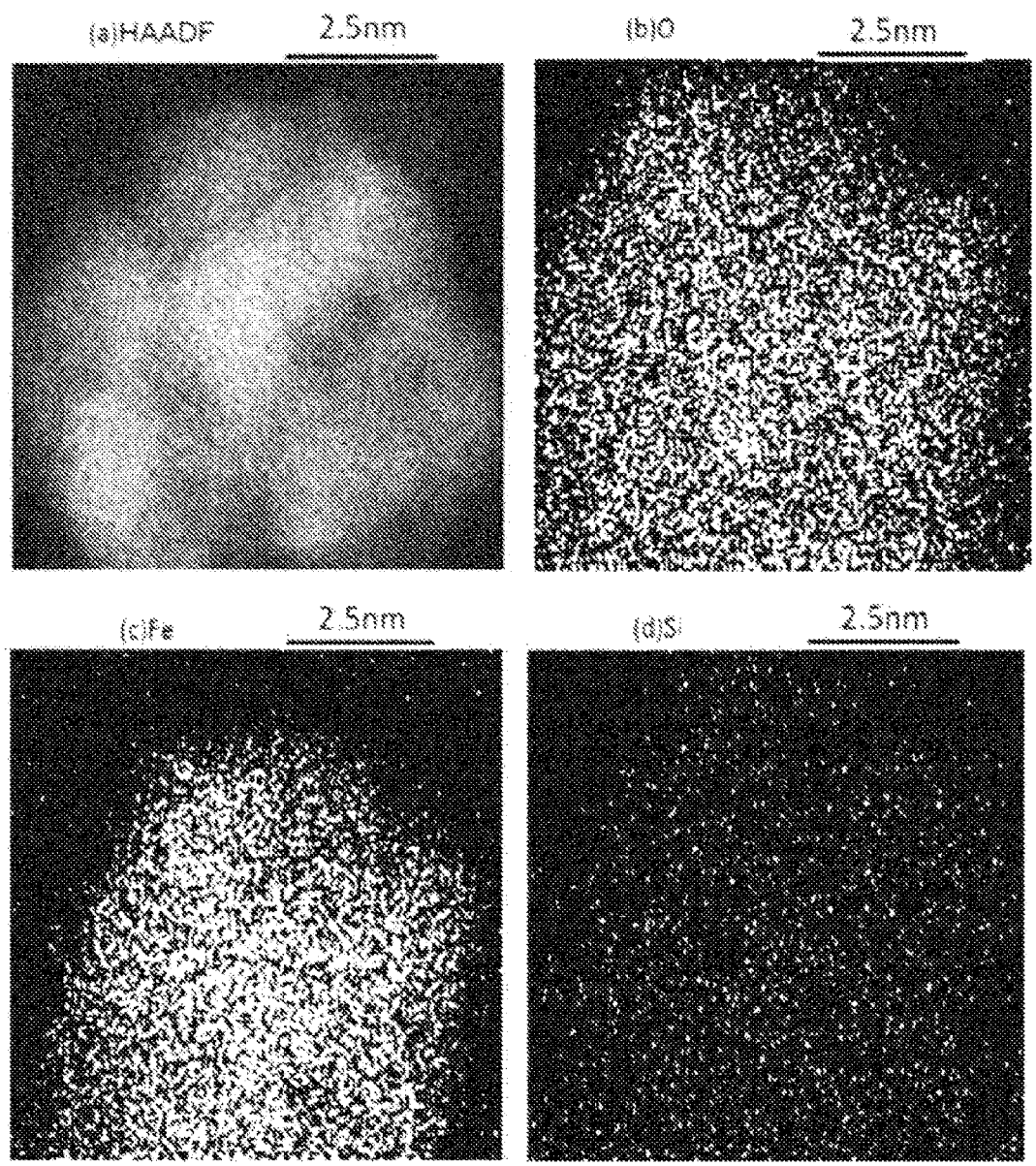
FIG. 2 shows an STEM mapping of the silicon oxide-coated iron oxide particles obtained in Example 1 of the present invention.

FIG. 1 shows a transmission electron microscopy (TEM) photograph of the silicon oxide-coated iron oxide particles obtained in Example 1 as described below. As shown in FIG. 1, core-shell type iron oxide particles wherein the entire surface of one iron oxide particle as a core is uniformly coated with silicon oxide, is observed, and a coating layer (shell) of silicon oxide having a thickness of about 1.37 nm on the entire surface of the core iron oxide particles is observed. FIG. 2 shows a scanning transmission electron microscopy (STEM) mapping result of the silicon oxide-coated iron oxide particles obtained in Example 1. In FIG. 2, (a) shows a mapping of a dark-field image (HADDF image), (b) shows a mapping of oxygen (O), (c) shows a mapping of iron (Fe), and (d) shows a mapping of silicon (Si). Regarding the particles observed in the HADDF image, distribution of oxygens (O) and silicons (Si) is observed in the entire particles, and distribution of iron (Fe) is observed in about 1.37 nm smaller area in radius compared with the particles. Especially, since iron oxide has photocatalytic activity, when at least a part of the surface of iron oxide is not coated with silicon oxide, iron oxide may absorb an ultraviolet ray to exhibit photocatalytic ability, and various components included in a paint and a coating film, such as a coloring material, a resin and a dispersing agent may be decomposed. Therefore, silicon oxide-coated iron oxide particles wherein at least a part of the surface of iron oxide is coated with silicon oxide, is used in the present invention. Coating may be performed by coating at least a part of the core iron oxide particles, and not entire core iron oxide particles. Furthermore, when the surface of iron oxide particle is coated with crystalline silicon oxide, the reflectivity for the light of the wavelength of 620 to 750 nm may be increased, due to its influence to the refractive index. Since at least a part of the surface of the iron oxide particles is coated with silicon oxide comprising amorphous silicon oxide in the present invention, the average reflectivity in the region of the wavelengths of 620 to 750 nm can be reduced to 25% or less, and performance when used in a paint can be improved. Further, a dispersion including iron oxide particles wherein at least a part of the surface of the iron oxide is coated with silicon oxide containing amorphous silicon oxide, can accomplish the above mentioned transmittance spectral properties and transparency, which is preferable. The above silicon oxide may be in the state of $SiO_2$, and also may be in the state wherein a part of oxygen is deficient like $SiO_{2-x}$.

Figure 3:
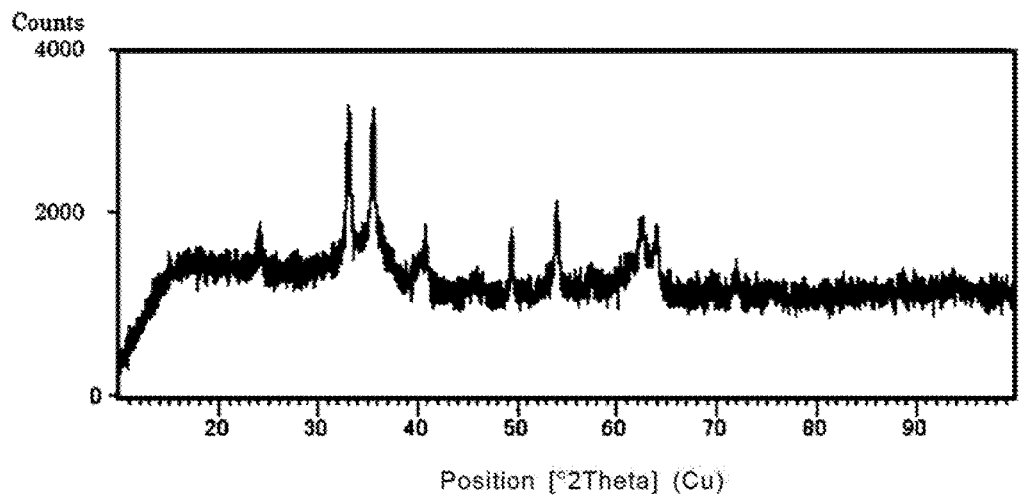
FIG. 3 shows an XRD measurement result of the silicon oxide-coated iron oxide particles obtained in Example 1 of the present invention.
Figure 4:
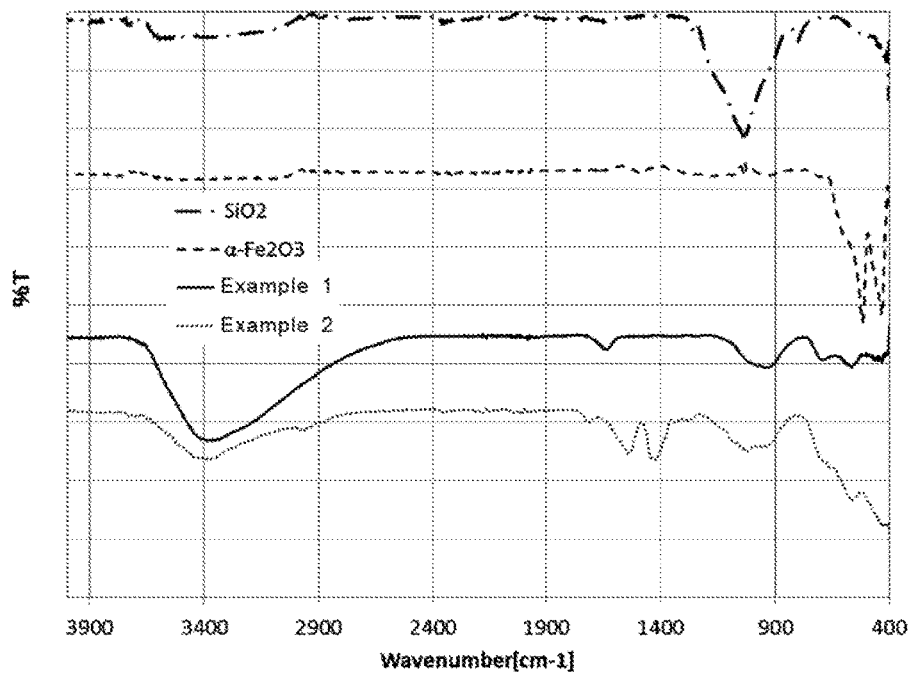
FIG. 4 shows FT-IR measurement results of the silicon oxide-coated iron oxide particles obtained in Example 1 and Example 2 of the present invention.

FIG. 3 shows an X-ray diffraction (XRD) measurement result of the silicon oxide-coated iron oxide particles obtained in Example 1 as described below. In the measurement result, peaks derived from the iron oxide ($\alpha$-$Fe_2O_3$) are observed, but no other peaks are observed. Further, FIG. 4 shows infrared absorption spectrum (FT-IR) measurement results of the silicon oxide-coated iron oxide particles obtained in Example 1 and the silicon oxide-coated iron oxide particles obtained in Example 2, wherein the silicon oxide-coated iron oxide particles obtained in Example 1 were provided with acetyl groups, together with FT-IR measurement results of silicon dioxide ($SiO_2$) and the iron oxide ($\alpha$-$Fe_2O_3$). As shown in FIG. 4, a broad peak around 950 $cm^{-1}$ was observed for the silicon oxide-coated iron oxide particles obtained in Example 1. This peak was not observed in the iron oxide ($\alpha$-$Fe_2O_3$), and the wave number of this peak is lower than that of the peak at around 1000 $cm^{-1}$ observed in $SiO_2$. Therefore, it is considered possible that the silicon oxide in the silicon oxide-coated iron oxide particles obtained in Example 1 is in the state of $SiO_2$ or in the state wherein a part of oxygen is deficient like $SiO_{2-X}$. Further, a broad peak from about 2900 $cm^{-1}$ to about 3600 $cm^{-1}$ derived from hydroxyl groups was observed. Also, in the FT-IR measurement result of the silicon oxide-coated iron oxide particles obtained in Example 2 wherein the silicon oxide-coated iron oxide particles obtained in Example 1 were provided with acetyl groups, the broad peak from about 2900 $cm^{-1}$ to about 3600 $cm^{-1}$ derived from hydroxyl groups is smaller, which was observed in the FT-IR measurement result of the silicon oxide-coated iron oxide particles obtained in Example 1, and peaks at about 1450 $cm^{-1}$ and about 1600 $cm^{-1}$ derived from acetyl groups were observed.

Namely, the silicon oxide-coated iron oxide particles obtained in Example 1 as described below is considered to be a silicon oxide-coated iron oxide particles wherein the surface is coated with amorphous silicon oxide.

And the silicon oxide-coated iron oxide particles obtained in Example 2 is considered to be prepared by addition of an acetyl group to a hydroxyl group contained in the silicon oxide-coated iron oxide particles obtained in Example 1, and to add an acetoxyl group to the silicon oxide-coated iron oxide particles.

Thus, in the present invention, FT-IR and XRD were measured for silicon oxide-coated iron oxide particles. It was verified that the silicon oxide is amorphous, by confirming peaks derived from silicon oxide in FT-IR measurement, and by not confirming peaks derived from silicone oxide in XRD measurement. In addition, it is also possible to verify that the silicon oxide is amorphous, by not confirming the crystal lattice derived from silicon oxide by STEM observation of silicon oxide-coated iron oxide particles.

In the present invention, the state of coating with silicon oxide on the iron oxide particles was confirmed by electron microscopy such as TEM or STEM.

Though the details are not clear, a silicon oxide-coated iron oxide particles of the present invention has (1) oxygen from the iron oxide particles, (2) iron from the iron oxide particles, (3) oxygen on the surface of the iron oxide particles, (4) silicon from the silicon oxide coating the surface of the iron particles, (5) oxygen from the silicon oxide coating the surface of the iron oxide particles. It is possible that a bond is formed between each element above, for example, the bonds: (1)-(2)-(3)-(4)-(5). Such bond may affect crystallinity of the surface of the iron oxide particles, or strain in the bond may occur, and so on, because silicon oxide coating at least a part of the surface of iron oxide comprises amorphous silicon oxide. Thus, color characteristics exhibited by iron oxide can be controlled. The inventors consider the above mechanism may be another possibility for control of color characteristics, particularly reflectivity, of a composition for a laminated coating film including silicon oxide-coated iron oxide particles of the present invention. Not particularly limited, the inventors consider that it is another possible factor for control of color characteristics of a silicon oxide-coated iron particle dispersion of the present invention, that the iron oxide particles are crystalline, and silicon oxide coating at least a part of the surface of the iron oxide particles contains amorphous one.

Further in the present invention, color characteristics of a composition for a laminated coating film containing the silicon oxide-coated iron oxide may be controlled by changing a functional group contained in the silicon oxide-coated iron oxide particles. Though the details are not clear, the inventors consider that color characteristics of a composition for a laminated coating film containing the silicon oxide-coated iron oxide can be controlled by controlling an element and a functional group bonding to the oxygen in above (3) or (5). For example, when hydrogen bonds to the oxygen in (3) or (5), hydroxyl groups are present on the surface of the silicon oxide-coated iron oxide particles. The hydroxyl group may be replaced by another functional group such as an acyl group and benzoyl group. Different types of functional groups have properties of absorption and vibration against a light of a specific wavelength respectively. The properties of absorption and vibration against a light on the surface of a silicon oxide-coated iron oxide particles can be changed by changing a functional group contained in the silicon oxide-coated iron oxide particles of the present invention, including a functional group bonding to the oxygen of above (3) or (5). Therefore, the present inventors consider that color characteristics of a composition for a laminated coating film containing a silicon oxide-coated iron oxide can be controlled by changing a functional group contained in a silicon oxide-coated iron oxide particles of the present invention.

Since influence of the fluorescence emission was considered, the fluorescence spectra were measured for silicon oxide-coated particles before and after changing the functional group contained in the silicon oxide-coated particles, using the fluorescence spectrophotometer (product name: FP-6500, JASCO Corporation), with excitation wavelength of 220 to 750 nm, in the measuring range of the fluorescence wavelength of 220 to 750 nm. No fluorescence was observed in both spectra.

Furthermore, since the particle diameter of the iron oxide particles constituting silicon oxide-coated iron oxide particles of the present invention as well as the particle diameter of the silicon oxide-coated iron oxide particles are minute, the surface area of the silicon oxide-coated iron oxide particles increases, and a coating rate of the silicon oxide to the total silicon oxide-coated iron oxide particles is increased. Thus, the inventors consider that it would be also a possible factor for control of the color characteristics, that the above bonds: oxygen-iron-oxygen-silicon-oxygen (functional group) are increased.

As shown in FIG. 5, the reflectivity of the silicon oxide-coated iron oxide particles obtained in Example 1 for the light of the wavelength of around 550 to 780 nm, is reduced as compared with that of the iron oxide particles obtained in Comparative Example 1. This shows the result that amorphous silicon oxide coating gives a change in color characteristics. Further, the reflectivity of the silicon oxide-coated iron oxide particles obtained in Example 2 for the light of the wavelength of around 550 to 780 nm, is increased more than that of the silicon oxide-coated iron oxide particles obtained in Example 1. This shows that the color characteristics change by addition of an acetyl group to the silicon oxide-coated iron oxide particles. This result indicates that the color characteristics change by changing a functional group contained in the particles. Also, the reflectivity of the silicon oxide-coated iron oxide particles obtained in Example 3 for the light of the wavelength of around 550 to 780 nm, is less than that of the silicon oxide-coated iron oxide particles obtained in Example 2, and is higher than that of the silicon oxide-coated iron oxide particles obtained in Example 1 (not shown in FIG). However, significant difference in reflectivity was not observed between the iron oxide particles of Comparative Example 1 without silicon oxide coating on their surface and the iron oxide aggregates of Comparative Example 2 with silicon oxide coating. Further, the reflectivity for the light of the wavelength of 550 to 780 nm of the silicon oxide-coated iron oxide particles obtained in Example 4 wherein an aggregate of iron oxide particles is coated with silicon oxide, and the particle diameter of the aggregate of iron oxide particles is 50 nm or less, is slightly higher than that of Example 1, and is lower than that of the silicon oxide-coated iron oxide particles as in Comparative Example 2 wherein an aggregate of iron oxide particles is coated with silicon oxide, and the particle diameter of the aggregate of iron oxide particles exceeds 50 nm. It was found that reflectivity could be controlled by a coating condition of the surface of iron oxide particles with the silicon oxide. On the other hand, it was found that the effect on color characteristics of the present invention was lowered when aggregates of iron oxide particles, particularly aggregates of iron oxide particles having more than 50 nm diameter were coated with silicon oxide.

For example, in case that silicon oxide-coated iron oxide particles of the present invention is used in a composition for a laminated coating film of the present invention, in particular a red-colored composition for a laminated coating film, the composition can express a deep red color, when the reflectivity of the silicon oxide-coated iron oxide particles for the light of the wavelength of around 550 to 780 nm is reduced as compared with that of the iron oxide particles obtained in Comparative Example 1, like the silicon oxide-coated iron oxide particles obtained in Examples 1 and 2. The composition can express a deeper red color, when the reflectivity for the light of the wavelength of around 550 to 780 nm is lower than that of the silicon oxide-coated iron oxide particles obtained in Example 2, like the silicon oxide-coated iron oxide particles obtained in Example 1. Thus, it is possible to use properly silicon oxide-coated iron oxide particles depending on a desired color and designability. Significant color change can be observed by visual inspection.

In the present invention, the reflectivity of the silicon oxide-coated iron oxide particles of the present invention for the light of the wavelength of around 550 to 780 nm, is reduced as compared with that of the iron oxide particles without silicon oxide coating. The effects by the reduced reflectivity of silicon oxide-coated iron oxide particles of the present invention at the wavelength of around 550 to 780 nm, are the followings in addition to the above mentioned effects. When a composition for a laminated coating film of the present invention is mixed to a paint for a clear coating film or a paint for a colored coating film to form a coating film, specifically in case that a color of the coated body is recognized by making a light pass through the a clear coating film and a colored coating film, and then by making the light reflected on the base metallic coating film pass through the clear coating film and colored coating film again, the transmittance of the silicon oxide-coated iron oxide particles of the present invention contained in the clear coating film and colored coating film for the light of the wavelength of 550 to 780 nm, is preferably higher, but the reflectivity is preferably lower. This is because, when the reflectivity is high, for example, the site which should be seen as a shade in the coating film or the coated body, exhibits a color, and then the effects providing color depth and shadowing to the coating film or coated body is lowered, and difference between highlight and shade is difficult to be obtained, and the problem that the coating film or coated body looks blurred occurs, which may impair designability of the product.

Color characteristics, particularly reflectivity, of iron oxide particles can be changed by selecting presence or absence of amorphous silicon oxide coating at least a part of the surface of iron oxide particles, and presence or absence of a functional group contained in silicon oxide-coated iron oxide particles, or acetyl group shown in the following Examples 1 and 2, to manufacture iron oxide particles.

A functional group contained in silicon oxide-coated iron oxide particles, refers to a functional group which is at least introduced to or coupled with silicon oxide-coated iron oxide particles. Color characteristics of silicon oxide-coated iron oxide particles, specifically reflectivity at the wavelength of around 550 to 780 nm can be controlled by changing a functional group. A functional group is believed to be present on the surface of the silicon oxide-coated iron oxide particles, but it may be present inside the silicon oxide-coated iron oxide particles. The functional group includes hydroxyl group contained in the silicon oxide-coated iron oxide particles, or a functional group substitutable with the hydroxyl group. A functional group substitutable with the hydroxyl group includes an acyl group such as acetyl group, benzoyl group and the like, an alkyl group such as methyl group, ethyl group and the like, and an alkyl silyl group, an aryl group and the like. Change of a functional group may be change of at least a part of functional groups contained in silicon oxide-coated iron oxide particles, or it may be change of all functional groups.

In silicon oxide-coated iron oxide particles of the present invention, the color characteristics of the composition for a laminated coating film is controlled by the existence of the amorphous silicon oxide coating at least a part of the surface of the iron oxide particles and the coating rate of the amorphous silicon oxide to the surface of the iron oxide particles. The existence of the amorphous silicon oxide coating at least a part of the surface of the iron oxide particles and the coating rate of the amorphous silicon oxide to the surface of the iron oxide particles make greater influences on the reflectivity of the silicon oxide-coated iron oxide particle dispersion at the wavelengths from 550 nm to 780 nm, than on the transmission spectrum of the dispersion wherein silicon oxide-coated iron oxide particles is dispersed in a liquid dispersion medium.

In silicon oxide-coated iron oxide particles of the present invention, a shape of the particles has smaller effects than the other factors described above, and thus the shape of the particles may be in various shapes. However, a substantially spherical shape is preferable, because the shape enables reduction of birefringence in the paint. Silicon oxide-coated iron oxide particles of the present invention are preferably substantially spherical particles, wherein a long diameter/short diameter ratio is from 1.0 to 3.0, preferably from 1.0 to 2.5, more preferably from 1.0 to 2.0. Silicon oxide-coated iron oxide particles of the present invention are preferably silicon oxide-coated iron oxide particles, wherein at least a part of the surface of iron oxide particles which are 1 nm or more and 50 nm or less is coated with silicon oxide.

(Manufacturing Method: Device)

A method of producing silicon oxide-coated iron oxide particles of the present invention includes, for example, a method wherein iron oxide particles are produced in the first microreactor, and at least a part of the surface of the iron oxide particles are coated with silicon oxide in the subsequent second microreactor; a method wherein iron oxide particles are produced in a batch vessel under a dilute system and the like, and continuously at least a part of the surface of the iron oxide particles are coated with silicon oxide under a dilute system, and the like; a method wherein iron oxide particles are produced by pulverization such as bead mill, and subsequently at least a part of the surface of the iron oxide particles are coated with silicon oxide under a dilute system, and the like. The apparatus and method as proposed by the present applicant and described in JP 2009-112892 may be also used. The apparatus described in JP 2009-112892 comprises a stirring tank having an inner peripheral surface which cross-section is circular, and a mixing tool attached to the stirring tank with a slight gap to the inner peripheral surface of the stirring tank, wherein the stirring tank comprises at least two fluid inlets and at least one fluid outlet; from one of the fluid inlets, the first fluid to be processed containing one of the reactants among the fluids to be processed is introduced into the stirring tank; from one fluid inlet other than the above inlet, the second fluid to be processed containing one of reactants different from the above reactant is introduced into the stirring tank through a different flow path; at least one of the stirring tank and the mixing tool rotates at a high speed relative to the other to let the above fluids be in a state of a thin film; and in the above thin film, the reactants contained in the first and second fluids to be processed are reacted. JP 2009-112892 further describes that three or more inlet tubes may be provided as shown in FIGS. 4 and 5 to introduce three or more fluids to be processed into the stirring tank.

In the present invention, it is preferable that production of iron oxide particles is preferably performed at least using a microreactor. It is preferable to use an apparatus using the same principle as the fluid processing apparatus described in Patent Literature 6, for production of iron oxide particles and for coating at least a part of the surface of the produced iron oxide particles with silicon oxide to form silicon oxide-coated iron oxide particles. Manufacturing iron oxide particles using a microreactor is preferable for controlling the color characteristics such as reflectivity, because distortion or the like on the crystallinity of the iron oxide particles hardly occurs by manufacturing those using a microreactor.

As an example of a method of producing silicon oxide-coated iron oxide particles of the present invention, it is preferable to use a method of producing silicon oxide-coated iron oxide particles, wherein iron oxide particles are precipitated in a mixed fluid of an iron oxide raw material liquid containing at least a raw material of iron oxide particles, and an iron oxide precipitation liquid containing at least iron oxide precipitation substance for precipitating iron oxide particles; and the mixed fluid containing the precipitated iron oxide particles are mixed with a silicon oxide raw material liquid containing at least a raw material of silicon oxide to coat at least a part of the surface of iron particles with silicon oxide.

A raw material of oxide iron oxide particles and a raw material of silicon oxide which are used in production of a silicon oxide-coated iron oxide particles of the present invention are not particularly limited. Any substances can be used as long as the substances become an iron oxide or silicon oxide in a manner such as a reaction, crystallization, precipitation or the like. In the present invention, hereinafter, the method above is referred to as precipitation.

A raw material of iron oxide particles includes, for example, elemental iron and an iron compound. An iron compound is not particular limited, but includes, for example, an iron salt, an iron oxide, an iron hydroxide, an iron hydroxide oxide, an iron nitride, an iron carbide, an iron complex, an iron organic salt, an iron organic complex, an iron organic compound, or a hydrate thereof, an organic solvate thereof and the like. An iron salt is not limited, but includes an iron nitrate, an iron nitrite, an iron sulfate, an iron sulfite, an iron formate, an iron acetate, an iron phosphate, an iron phosphite, an iron hypophosphite, an iron chloride, an oxy iron, an iron acetylacetonate, or a hydrate thereof, an organic solvate thereof and the like. An organic compound includes an iron alkoxide and the like. These iron compounds may be used alone, or a mixture of a plurality of these iron compounds may be used as a raw material of iron oxide particles. Specific examples include, for example, iron(III) chloride, iron(II) chloride, iron(II) nitrate, iron(III) sulfate, iron acetylacetonate and a hydrate thereof and the like.

A raw material of silicon oxide includes a silicon oxide, a silicon hydroxide, other compounds such as a silicon salt and a silicon alkoxide, and a hydrate thereof. Not particularly limited, it includes phenyltrimethoxysilane, methyltrimethoxysilane, methyltriethoxysilane, 3-glycidoxypropyl-trimethoxysilane, 3-trifluoropropyl-trimethoxysilane, methacryloxypropyltriethoxysilane, tetramethoxysilane (TMOS), tetraethoxysilane (TEOS), and an oligomeric condensate of TEOS, for example, ethyl silicate 40, tetraisopropylsilane, tetrapropoxysilane, tetraisobutoxysilane, tetrabutoxysilane, and a similar material thereof. Further as a raw material of silicon oxide, another siloxane compound, bis(triethoxysilyl)methane, 1,9-bis(triethoxysilyl)nonane, diethoxydichlorosilane, triethoxychlorosilane and the like may be used.

Further, when a raw material of iron oxide particles or a raw material of silicon oxide is a solid, it is preferable to use a raw material of iron oxide particles or a raw material of silicon oxide in a molten state, or in a state of being mixed or dissolved in a solvent described below, including a dispersion state. Even when a raw material of iron oxide particles or a raw materials of silicon oxide is a liquid or gas, it is preferable to use them in a state of being mixed or dissolved in a solvent described below, including a dispersion state. Regarding a raw material of iron oxide particles, in case of using only a raw material that can become iron oxide particles, for example, an elemental iron and an iron compound, iron oxide particles containing an element iron as an element other than oxygen may be produced. Further, regarding a raw material of iron oxide particles, in case of using one or more raw materials of iron oxide particles in addition to a raw material that can become iron oxide particles, a composite iron oxide containing one or more elements other than elemental iron as an element other than oxygen may be produced. An element other than elemental iron is not particularly limited, and every element described in the chemical periodic table may be applied. As a material of an iron oxide other than a raw material that can become iron oxide particles, a simple substance or a compound of every element described in the chemical periodic table except for elemental iron may be used. Further, the invention can be performed when these iron oxide raw material liquid and silicon oxide raw material liquid include those in a state of the condition such as dispersion or slurry.

In the present invention, iron oxide particles are preferably α-$Fe_2O_3$ (hematite). Therefore, an iron ion contained in the raw material of iron oxide particles is preferably $Fe^{3+}$. It is preferable to use a substance that generates $Fe^{3+}$ ion in a solution as a raw material of iron oxide particles. However, a raw material of iron oxide particles may be prepared by dissolving a substance producing a $Fe^{2+}$ ion in a solvent, followed by using a means of changing the $Fe^{2+}$ ion to a $Fe^{3+}$ ion by an oxidizing acid such as nitric acid, and the like.

An iron oxide precipitation substance is not particularly limited as long as the substance can make a raw material of iron oxide particles contained in an iron oxide raw material liquid be precipitated as iron oxide particles, and can make a raw material of silicon oxide contained in an silicon oxide raw material liquid be precipitated as silicon oxide. For example, an acidic substance or a basic substance may be used. It is preferable to use an iron oxide precipitation substance at least in a state that the substance is mixed, dissolved or molecularly dispersed in a solvent described below.

A basic substance includes a metal hydroxide such as sodium hydroxide and potassium hydroxide, a metal alkoxide such as sodium methoxide and sodium isopropoxide, an amine compound such as triethylamine, diethylaminoethanol and diethylamine, ammonia and the like.

An acidic substance includes an inorganic acid such as aqua regia, hydrochloric acid, nitric acid, fuming nitric acid, sulfuric acid, fuming sulfuric acid, and an organic acid such as formic acid, acetic acid, chloroacetic acid, dichloroacetic acid, oxalic acid, trifluoroacetic acid, trichloroacetic acid and the like.

A solvent used in preparation of an iron oxide raw material liquid, an iron oxide precipitation solvent and silicon oxide raw material liquid, includes, for example, water, an organic solvent, or a mixed solvent of a plurality of these solvents. The water includes tap water, ion exchange water, pure water, ultrapure water, RO water and the like. The organic solvent includes, an alcohol solvent, an amide solvent, a ketone solvent, an ether solvent, an aromatic compound solvent, carbon disulfide, an aliphatic compound solvent, a nitrile solvent, a sulfoxide solvent, a halogen compound solvent, an ester solvent, an ionic liquid, a carboxylic acid compound, a sulfonic acid compound and the like. Each of the above solvents may be used alone, or a plurality of them may be mixed and used. An alcohol solvent includes a monohydric alcohol such as methanol and ethanol, a polyol such as ethylene glycol and propylene glycol, and the like. Further, if necessary, the above acidic substance or the above basic substance may be mixed with an iron oxide raw material liquid or a silicon oxide raw material liquid, as long as it does not adversely affect production of silicon oxide-coated iron oxide particles.

(Dispersing Agent and the Like)

In the present invention, various dispersing agents or surfactants may be used depending on a purpose or necessity, as long as they do not adversely affect production of silicon oxide-coated iron oxide particles. Not particularly limited, as a dispersing agent or a surfactant, various generally used commercial products or products, and newly synthesized products and the like may be used. As an example, a dispersing agent such as an anionic surfactant, a cationic surfactant, a nonionic surfactant, and various polymers and the like may be used. These may be used alone or two or more thereof may be used in combination. The surfactant and dispersing agent may be contained in at least one fluid of the iron oxide raw material liquid, iron oxide precipitation solvent, and silicon oxide raw material liquid. In addition, the surfactant and dispersing agent may be contained in another fluid different from the iron oxide raw material liquid, iron oxide precipitation solvent, and silicon oxide raw material liquid.

A method of changing a functional group contained in silicon oxide-coated iron oxide particles of the present invention is not particularly limited. It may be performed by dispersing silicon oxide-coated iron oxide particles in a desired solvent, and adding a substance containing a functional group into the dispersion liquid, followed by a processing such as stirring. It may be also performed by mixing a fluid containing silicon oxide-coated iron oxide particles and a fluid containing a substance containing a functional group using a microreactor described above.

A substance having a functional group is a substance containing a functional group that can be substituted with a hydroxyl group contained in silicon oxide-coated iron oxide particles. The examples include an acylating agent such as acetic anhydride and propionic anhydride, a methylation agent such as dimethyl sulfate and dimethyl carbonate, and a silane coupling agent such as chlorotrimethylsilane and methyl trimethoxysilane, and the like.

Not particularly limited, a composition for a laminated coating film of the present invention may be applied to those described in Patent Literature 3 or 4, and various painting compositions such as a solvent-based paint, a water-based paint. A painting composition may further comprise in addition to various resin components, if necessary, additives such as pigments, dyes, wetting agents, dispersing agents, color separation inhibitors, leveling agents, viscosity modifiers, anti-skinning agents, anti-gelling agents, antifoaming agents, thickeners, anti-sagging agents, antifungal agents, ultraviolet absorbers, film-forming assistant agents, surfactants, if necessary. A resin component includes polyester resins, melamine resins, phenol resins, epoxy resins, vinyl chloride resins, acrylic resins, urethane resins, silicone resins, fluorine resins and the like. A coated body which a paint containing a composition for a laminated coating film of the present invention is applied to, may be a multilayer coated body composed of plurality of painting compositions, or a single layer coated body composed of a single painting composition. A composition for a laminated coating film of the present invention may be performed by adding it to a paint containing a pigment, or to a paint such as a clear paint.

Color of a coated body includes a red color such as color having a hue from RP to YR in the Munsell hue circle; a yellow to green color such as a color having a hue from Y to BG in the Munsell hue circle; a blue to purple color such as a color having a hue from B to P in the Munsell hue circle (each of these colors includes a metallic color), but the color is not particularly limited to these colors, and may be a color of any hue. The colors can be suitably mixed in a composition for a laminated coating film used in a coated body. As a pigment or dye optionally included in a composition for a laminated coating film, various pigments and dyes may be used, and for example, all pigments and dyes registered in the color index may be used. Among these colors, a pigment or dye constituting a red color includes, for example, a pigment or dye classified into C. I. Pigment Red in the Color Index, a pigment or dye classified into C. I. Pigment Violet or C. I. Pigment Orange in the Color Index; a pigment constituting a yellow color includes, for example, a pigment or dye classified into C. I. Pigment Yellow; a pigment constituting a green color includes, for example, a pigment or dye classified into C. I. Pigment Green; a pigment constituting a blue color includes, for example, a pigment or dye classified into C. I. Pigment Blue; a pigment constituting a white color includes, for example, a pigment or dye classified into C. I. Pigment White, and the like. More specific examples of a pigment or dye constituting a red color include a quinacridone pigment such as C. I. Pigment Red 122 and C. I. Violet 19; a diketopyrrolopyrrole pigment such as C. I. Pigment Red 254 and C. I. Pigment Orange73; a naphthol pigment such as C. I. Pigment Red 150 and C. I. Pigment Red 170; a perylene pigment such as C. I. Pigment Red 123 and C. I. Pigment Red 179; and an azo pigment such as C. I. Pigment Red 144, and the like. These pigments and dyes may be used alone, or a plurality of these may be mixed and used. Silicon oxide-coated iron oxide particles of the present invention may be also mixed in a composition for a laminated coating film alone without mixing with the above pigments and dyes and the like.

When a composition for a laminated coating film of the present invention comprises a perylene pigment such as C. I. Pigment Red 123 and C. I. Pigment Red 179, a coated body can be prepared which has high chroma and a large difference between highlight and shade. Thus, it is preferable particularly in case of a red coating material.

EXAMPLE

Hereinafter, the present invention is explained in more detail with reference to Examples, but the present invention is not limited only to these examples.

Example 1

The iron oxide raw material liquid, the iron oxide precipitation solvent, and the silicon oxide raw material liquid were prepared using the high-speed rotary dispersion emulsification apparatus CLEAMIX (product name: CLM-2.2 S, M. Technique Co., Ltd.). Specifically, based on the formulation of the iron oxide raw material liquid shown in Example 1 of Table 1, the components of the iron oxide raw material liquid were mixed homogeneously by stirring using CLEARMIX at preparation temperature of 40° C. and at the rotor rotational speed of 20000 rpm for 30 min to prepare the iron oxide raw material liquid. Based on the formulation of the iron oxide precipitation solvent shown in Example 1 of Table 1, the components of the iron oxide precipitation solvent were mixed homogeneously by stirring using CLEARMIX at preparation temperature of 45° C. and at the rotor rotational speed of 15000 rpm for 30 min to prepare the iron oxide precipitation solvent. Furthermore, based on the formulation of the silicon oxide raw material liquid shown in Example 1 of Table 1, the components of the silicon oxide raw material liquid were mixed homogeneously by stirring using CLEARMIX at preparation temperature of 20° C. and at the rotor rotational speed of 6000 rpm for 10 min to prepare the silicon oxide raw material liquid.

Regarding the substances represented by the chemical formula and abbreviations set forth in Table 1, 97 wt % $H_2SO_4$ is concentrated sulfuric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3 \cdot 9H_2O$ is iron nitrate nonahydrate (Kanto Chemical Co., Inc.).

Then, the prepared iron oxide raw material liquid, the iron oxide precipitation solvent oxide and the silicon oxide raw material liquid were mixed using the fluid processing apparatus described in Patent Literature 6 filed by the present applicant. Here, the fluid processing apparatus described in Patent Literature 6 is an apparatus described in FIG. 1(B) of Patent Literature 6, wherein the openings d20 and d30 of the second and third introduction parts have concentric annular shapes which are surrounding the central opening of the processing surface 2 which is a ring-shaped disc, which was used. Specifically, the iron oxide raw material liquid as liquid A was introduced from the first introduction part d1 into the space between the processing surfaces 1 and 2, and while driving the processing member 10 at a rotational speed of 1130 rpm, the iron oxide precipitation solvent as liquid B was introduced from the second introduction part d2 into the space between the processing surfaces 1 and 2, and the iron oxide raw material liquid and the iron oxide precipitation solvent were mixed in the thin film fluid, to let the core iron oxide particles be precipitated in the space between the processing surfaces 1 and 2. Then, the silicon oxide raw material liquid as liquid C was introduced from the third introduction part d3 into the space between the processing surfaces 1 and 2, and liquid C was mixed with a mixed fluid containing the core iron oxide particles in the thin film fluid. Silicon oxide was precipitated on the surface of the core iron oxide particles. The discharge liquid containing the silicon oxide-coated iron oxide particles (hereinafter, the silicon oxide-coated iron oxide particle dispersion liquid) was discharged from the space between the processing surfaces 1 and 2 of the fluid processing apparatus. The silicon oxide-coated iron oxide particle dispersion liquid was collected in the beaker b through the vessel v.

Table 2 shows the operating conditions of the fluid processing apparatus. The introduction temperatures (liquid sending temperatures) and the introduction pressures (liquid sending pressures) of liquid A, liquid B and liquid C shown in Table 2 were measured using a thermometer and a pressure gauge provided in a sealed inlet path leading to the space between the processing surfaces 1 and 2 (the first introduction part d1, the second introduction part d2 and the third introduction part d3). The introduction temperature of liquid A shown in Table 2 is the actual temperature of liquid A under the introduction pressure in the first introduction part d1. Similarly, the introduction temperature of liquid B shown in Table 2 is the actual temperature of liquid B under the introduction pressure in the second introduction part d2. The introduction temperature of liquid C shown in Table 2 is the actual temperature of liquid C under the introduction pressure in the third introduction part d3.

For the pH measurement, the pH meter, model number D-51 manufactured by HORIBA Ltd. was used. The pH of liquid A, liquid B and liquid C were measured at room temperature prior to introduction into the fluid processing apparatus. Further, it is difficult to measure the pH of the mixed fluid immediately after mixing the iron oxide raw material liquid and the iron oxide precipitation solvent, and the pH of the mixed fluid immediately after mixing the mixed fluid containing the core iron oxide particles and the silicon oxide raw material liquid. Therefore, the silicon oxide-coated iron oxide particle dispersion liquid was discharged from the apparatus and collected in a beaker b, and the pH of the liquid was measured at room temperature.

Dry powders and wet cake samples were produced from the silicon oxide-coated iron oxide particle dispersion liquid which was discharged from the fluid processing apparatus, and collected in the beaker. The manufacturing method was conducted according to a conventional method of this type of processing. The discharged silicon oxide-coated iron oxide particle dispersion liquid was collected, and the silicon oxide-coated iron oxide particles were settled, and the supernatant was removed. Thereafter, the silicon oxide-coated iron oxide particles were washed and settled three times repetitively with the mixed solvent of 100 parts by weight of pure water and 100 parts by weight of methanol, and then, were washed and settled three times repetitively with pure water. A part of the finally obtained wet cake of the silicon oxide-coated iron oxide particles was dried at 25° C. at −0.10 MPaG for 20 hours to obtain the dry powders. The rest was the wet cake sample.

(Preparation of TEM Observation Sample and Preparation of STEM Observation Sample)

A part of the wet cake samples of the silicon oxide-coated iron oxide particles after the washing process obtained in Examples was dispersed in propylene glycol, and further was diluted to 100-fold by isopropyl alcohol (IPA). The resulting diluted liquid was dropped to a collodion membrane or a micro grid, and dried to prepare a TEM observation sample or an STEM observation sample.

(Transmission Electron Microscopy and Energy Dispersive X-Ray Analyzer: TEM-EDS Analysis)

For observation and quantitative analysis of the silicon oxide-coated iron oxide particles by TEM-EDS analysis, the transmission electron microscopy SEM-2100 (JEOL Ltd.) equipped with the energy dispersive X-ray analyzer JED-2300 (JEOL Ltd.) was used. The observation condition was the acceleration voltage of 80 kV, and the observation magnification of 10,000 times or more. The particle diameters (D) of Examples 1 to 3 were primary particle diameters, and were calculated from the maximum distance between two points on the outer periphery of the silicon oxide-coated iron oxide particles, and the average value of the measured particle diameters of 100 particles was shown. Also the core particle diameter (Dc) of Examples 1 to 3 were primary particle diameters of the iron oxide particles, and were calculated from the maximum distance between two points on the outer periphery of the core iron oxide particles in the silicon oxide-coated iron oxide particles, and the average value of the measured core particle diameters of 100 particles was shown. Also EDS analysis on one particle was performed, and a molar ratio of $SiO_2/Fe_2O_3$ was calculated by conversion from a molar ratio between the elements contained in the core iron oxide particles and the elements contained in the shell silicon oxide, and the average value of 10 particles was shown. The thickness of the shell silicon oxide (hereinafter referred to as the thickness of the shell layer) was measured. Four thickness was measured for one particle, and the average value of the measured thickness of 10 particles was described in the item "coating thickness" in Table 2. Hereinafter, the core iron oxide particles are also referred to as a core, and the shell silicon oxide is also referred to as a shell or a shell layer.

(Scanning Transmission Electron Microscopy and Energy Dispersive X-Ray Analyzer: STEM-EDS Analysis)

For the mapping and quantification of elements contained in the silicon oxide-coated iron oxide particles by STEM-EDS analysis, the atomic resolution analytical electron microscopy JEM-ARM200F (JEOL Ltd.) equipped with the energy dispersive X-ray analyzer Centurio (JEOL Ltd.) was used. The observation condition was the acceleration voltage of 80 kV and the observation magnification of 50,000 times or more, and a beam diameter of 0.2 nm was used for analysis.

(X-Ray Diffraction Measurement)

For the X-ray diffraction (XRD) measurement, the powder X-ray diffractometer Empyrean (Spectris Co., Ltd., PANalytical Division) was used. The measurement condition was measurement range of 10 to 100 [° 2Theta], Cu anticathode, tube voltage of 45 kV, tube current of 40 mA, and scanning speed of 0.3°/min. The XRD was measured using the dry powder of the silicon oxide-coated iron oxide particles obtained in each Example.

(FT-IR Measurement)

For the FT-IR measurement, the Fourier transform infrared spectrophotometer FT/IR-4100 (JASCO Corporation) was used. The measurement condition was the resolution of 4.0 cm$^{-1}$ and accumulated number of 1024 times, using an ATR method.

(Transmission Spectrum)

For the transmission spectrum, the ultraviolet-visible absorption spectrophotometer (product name: UV-2450, Shimadzu Corporation) was used. The measurement range was from 200 nm to 800 nm, and the sampling rate was 0.2 nm, and the measurement speed was slow speed.

For the transmission spectrum, the dispersion liquids prepared by dispersing the silicon oxide-coated iron oxide of Examples and Comparative Examples except for Example 2 in propylene glycol at a $Fe_2O_3$ concentration of 0.05 wt % were used as a measurement sample. The dispersion liquid prepared by dispersing the silicon oxide-coated iron oxide of Example 2 in butyl acetate dispersion at a $Fe_2O_3$ concentration of 0.05 wt % was used as a measurement sample.

(Haze Value Measurement)

For the haze value measurement, the haze value meter (Model HZ-V3, Suga Test Instruments Co., Ltd.) was used. The optical condition was the double-beam method and D65 light as a light source which corresponds to JIS K 7136 and JIS K 7361. A liquid cell of thickness of 1 mm was used for measurements, and the dispersed liquids described below were measured.

(Reflection Spectrum)

For the reflection spectrum, the ultraviolet-visible-near infrared spectrophotometer (product name: SolidSpec-3700, Shimadzu Corporation) was used. Measurement range was 250 to 2500 nm, and the sampling rate was 2.0 nm, and the measurement speed was medium speed, and measurement method was a double beam photometry. Total reflection measurement for measuring diffuse reflection and specular reflection was performed. For a background measurement (baseline) in measuring powders, the standard white plate (product name: Spectralon™, Labsphere Inc.) was used. The reflection spectrum was measured using the dry powders of the silicon oxide-coated iron oxide particles in each Example. The simple average value was calculated from the reflectivity at each measurement wavelength in the wavelength range of 620 to 750 nm to obtain the average reflectivity.

TABLE 1

Example 1

| Formulation of the 1st fluid (liquid A) Iron oxide raw material liquid | | | Formulation of the 2nd fluid (liquid B) Iron oxide precipitation solvent | | | | Formulation of the 3rd fluid (liquid C) — | | | |
|---|---|---|---|---|---|---|---|---|---|---|
| Formulation [wt %] | | | Formulation [wt %] | | | | Formulation [wt %] | | | |
| Raw material [wt %] | Raw material [wt %] | pH | Raw material [wt %] | Raw material [wt %] | pH | pH [° C.] | Raw material [wt %] | Raw material [wt %] | Raw material [wt %] | pH [° C.] |
| $Fe(NO_3)_3$ $9H_2O$ [2.00 wt %] | Pure water [98.00 wt %] | 1.8 26.6 | NaOH [9.00 wt %] | Pure water [91.00 wt %] | >14 | — | Pure water [92.89 wt %] | 97 wt % $H_2SO_4$ [5.11 wt %] | TEOS [2.00 wt %] | <1 — |

TABLE 2

Example 1

| Introduction flow rate [ml/min] | | | Introduction temperature (liquid sending temperature) [° C.] | | | Introduction pressure (liquid sending pressure) [MPaG] | | | Discharged liquid | |
|---|---|---|---|---|---|---|---|---|---|---|
| Liquid A | Liquid B | Liquid C | Liquid A | Liquid B | Liquid C | Liquid A | Liquid B | Liquid C | pH | Temperature [° C.] |
| 400 | 50 | 100 | 142 | 86 | 89 | 0.451 | 0.50 | 0.50 | 12.14 | 32.9 |

| Coating thickness [nm] | Shell/Core $SiO_2/Fe_2O_3$ Molar ratio | | Particle diameter (D) [nm] | Core particle diameter (Dc) [nm] | D/Dc |
|---|---|---|---|---|---|
| | Calcurated value | EDS | | | |
| 1.37 | 0.97 | 0.97 | 8.20 | 5.46 | 150.2% |

The molar ratios (shell/core) described in Table 2 and Table 4 are the ratio of the oxides of the elements, which the molar ratio of the elements calculated by the TEM-EDS analysis on one silicon oxide-coated iron oxide particle is converted into. For example, the molar ratio (shell/core, $SiO_2/Fe_2O_3$) in Example 1 of Table 2 is the value of $SiO_2/Fe_2O_3$ converted from the molar ratio of Si/Fe calculated by with TEM-EDS analysis on one silicon oxide-coated iron oxide particle. Table 2 shows the average molar ratio ($SiO_2/Fe_2O_3$) of 10 particles together with its calculated value. The calculated value was calculated from the Fe concentration in the iron oxide raw material liquid for core and its introduction flow rate, and the Si concentration in the silicon oxide raw material liquid for shell and its introduction flow rate.

FIG. 1 shows a TEM photograph of the silicon oxide-coated iron oxide particles obtained in Example 1. Core-shell type iron oxide particles wherein the core was one iron oxide particle, and the entire surface of the core was uniformly coated with silicon oxide, were observed, and a coating layer (shell) of silicon oxide having a thickness of about 1.37 nm on the entire surface of the core iron oxide particle was observed. FIG. 2 shows a mapping result using STEM of the silicon oxide-coated iron oxide particles obtained in Example 1. In FIG. 2, (a) shows a mapping of a dark-field image (HADDF image), (b) shows a mapping of oxygen (O), (c) shows a mapping of iron (Fe), and (d) shows a mapping of silicon (Si). Regarding the observed particles in the HADDF image, distribution of oxygens (O) and silicons (Si) in the entire particles was observed, and distribution of iron (Fe) in about 1.37 nm smaller area in radius compared with the particles was observed. D/Dc was 150.2%.

Example 2

The following process was performed to impart acetyl groups to the silicon oxide-coated iron oxide particles obtained in Example 1. First, 1 part by weight of the silicon oxide-coated iron oxide particles obtained in Example 1 was added to 99 parts by weight of propylene glycol, and dispersed using the high-speed rotary dispersion emulsification apparatus CLEARMIX (product name: CLM-2.2 S, M technique Co., Ltd.) at 65° C. at the rotor rotation speed of 20000 rpm for 1 hour, to prepare a dispersion. To the obtained propylene glycol dispersion of the silicon oxide-coated iron oxide particles, were added 2 parts by weight of pyridine and 1 part by weight of acetic anhydride relative to 1 part by weight of the silicon oxide-coated iron oxide particles, and were dispersed using the above high-speed rotary dispersion emulsification apparatus at 65° C. at a rotor rotational speed of 20000 rpm for 1 hour. The resulting processed liquid was centrifuged at the condition of 26,000 G for 15 min. and the supernatant was separated to obtain the precipitates. A part of the precipitates was dried at −0.10 MPaG at 25° C. for 20 hours to obtain the dried powders. As a result of TEM observation, the core particle diameter (Dc) of the silicon oxide-coated iron oxide particles obtained in Example 2 was 5.47 nm, and the particle diameter (D) was 8.19 nm. Thus, it was confirmed that the particle diameter was substantially the same to that in Example 1. D/Dc was 149.7%.

In the XRD measurement result of the silicon oxide-coated iron oxide particles obtained in Example 1 as shown in FIG. 3, peaks derived from the iron oxide ($\alpha$-$Fe_2O_3$) were observed, but no other peaks were observed. The XRD measurement results of the silicon oxide-coated iron oxide particles obtained in Example 2 were similar to those of the silicon oxide-coated iron oxide particles in Example 1. Further, FIG. 4 shows FT-IR measurement results of the silicon oxide-coated iron oxide particles obtained in Example 1 and the silicon oxide-coated iron oxide particles provided with acetyl groups obtained in Example 2, together with FT-IR measurement results of silicon dioxide ($SiO_2$) and an iron oxide ($\alpha$-$Fe_2O_3$). As shown in FIG. 4, a broad peak around 950 $cm^{-1}$ was observed for the silicon oxide-coated iron oxide particles obtained in Example 1. This peak was not observed in the iron oxide ($\alpha$-$Fe_2O_3$), and the wave number of this peak is lower than that of the peak at around 1000 $cm^{-1}$ observed in $SiO_2$. Therefore, it is considered possible that the silicon oxide in the silicon oxide-coated iron oxide particles obtained in Example 1 is in the state of $SiO_2$ or in the state wherein a part of oxygen is deficient like $SiO_{2-x}$. Further, a broad peak from about 2900 $cm^{-1}$ to about 3600 $cm^{-1}$ derived from hydroxyl groups was observed. Also, in the FT-IR measurement result of the silicon oxide-coated iron oxide particles provided with acetyl groups obtained in Example 2, the broad peak from about 2900 $cm^{-1}$ to about 3600 $cm^{-1}$ derived from hydroxyl groups is smaller, which was observed in the FT-IR measurement result of the silicon oxide-coated iron oxide particles obtained in Example 1, and peaks at about 1450 $cm^{-1}$ and about 1600 $cm^{-1}$ derived from acetyl groups were observed.

Namely, the silicon oxide-coated iron oxide particles obtained in Example 1 is a silicon oxide-coated iron oxide particles wherein the surface is coated with amorphous silicon oxide. And the silicon oxide-coated iron oxide particles obtained in Example 2 is considered to be prepared by addition of an acetyl group to the silicon oxide-coated iron oxide particles obtained in Example 1 by replacing a hydroxyl group contained in the silicon oxide-coated iron oxide particles with an acetyl group.

Comparative Example 1

In Comparative Example 1, the iron oxide particles which surface was not coated by silicon oxide was prepared in the same manner as in Example 1 except that the silicon oxide raw material liquid as liquid C was not used (except the liquid C condition). TEM observation, reflection spectrum, XRD, transmission spectrum and haze value were measured in a similar manner as in Example 1. The particle diameter measured by the same method as for the core particle diameter in Example 1 was 6.40 nm. From the XRD measurement result, only the peak of iron oxide was detected. The pH of the discharged liquid was 13.89 (measurement temperature 29.6° C.). The resulting iron oxide particles in the iron oxide particle dispersion liquid had already been aggregated.

Example 3

In Example 3, the silicon oxide-coated iron oxide particles were prepared in the same manner as in Example 1 except for using an apparatus described in JP 2009-112892, and using a method of mixing and reacting liquid A (iron oxide raw material liquid), liquid B (iron oxide precipitation solvent) and liquid C (silicon oxide raw material liquid). Here, the apparatus of JP 2009-112892 is an apparatus described in FIG. 4 of JP 2009-112892, wherein the inner diameter of the stirring tank is uniform and is 420 mm, and the gap between the outer end of the mixing tool and the inner peripheral surface of the stirring tank is 1 mm, and the rotor rotational speed of the stirring blade was the same as the rotor rotational speed (1130 rpm) of the processing member 10 in the fluid processing apparatus used in Example 1. Further, liquid A was introduced into the stirring tank, and liquid B was added, mixed and reacted in the thin film consisting of liquid A that was crimped to the inner peripheral surface of the stirring tank. Then, liquid C was added, mixed and reacted in the thin film consisting of the mixed liquid of liquid A and liquid B crimped to the inner peripheral surface of the stirring tank. As a result of TEM observation, the core was one iron oxide particle, and the silicon oxide-coated iron oxide particles wherein a part of the surface of the core was coated with silicon oxide, was observed. A coating layer (shell) of silicon oxide having a thickness of from 1.0 nm to 2.0 nm on the surface of the core iron oxide particle was observed. A mapping using STEM of the silicon oxide-coated iron oxide particles obtained in Example 3, was done in the same manner as in Example 1. Regarding the observed particles in the HADDF image, distribution of oxygens (O) in the entire particles was observed, and distribution of iron (Fe) in about 1.0 nm to 2.0 nm smaller area in radius compared with the particles was observed, and distribution of silicons (Si) mainly in the coating layers was observed. The particle diameter (D) was 16.9 nm, the thickness of silicon oxide of a shell (coating thickness) was from 1.0 nm to 2.0 nm, and D/Dc of the silicon oxide-coated iron oxide particles was from 113.4% to 131.0%. From the XRD measurement results of the silicon oxide-coated iron oxide particles in Example 3, peaks derived from iron oxide ($Fe_2O_3$) were observed, and no other peaks were observed.

Example 4

The iron oxide raw material liquid, the iron oxide precipitation solvent, and the silicon oxide raw material liquid were prepared using the high-speed rotary dispersion emulsification apparatus CLEAMIX (product name: CLM-2.2 S, M. Technique Co., Ltd.). Specifically, based on the formulation of the iron oxide raw material liquid shown in Example 4 of Table 3, the components of the iron oxide raw material liquid were mixed homogeneously by stirring using CLEARMIX at preparation temperature of 40° C. and at the rotor rotational speed of 20000 rpm for 30 min to prepare the iron oxide raw material liquid. Based on the formulation of the iron oxide precipitation solvent shown in Example 4 of Table 3, the components of the iron oxide precipitation solvent were mixed homogeneously by stirring using CLEARMIX at preparation temperature of 45° C. and at the rotor rotational speed of 15000 rpm for 30 min to prepare iron oxide precipitation solvent. Furthermore, based on the formulation of the silicon oxide raw material liquid shown in Example 4 of Table 3, the components of the silicon oxide raw material liquid were mixed homogeneously by stirring using CLEARMIX at preparation temperature of 20° C. and at the rotor rotational speed of 6000 rpm for 10 min to prepare the silicon oxide raw material liquid.

Regarding the substances represented by the chemical formula and abbreviations set forth in Table 3, 97 wt % $H_2SO_4$ is concentrated sulfuric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3 \cdot 9H_2O$ is iron nitrate nonahydrate (Kanto Chemical Co., Inc.).

the surface of the aggregates of iron oxide particles was observed. Regarding the state of the coating, it was also observed that the aggregates were mainly uniformly coated, but a part of the aggregates were not coated. Further, the

TABLE 3

Example 4

| Formulation of the 1st fluid (liquid A) Iron oxide raw material liquid | | | | Formulation of the 2nd fluid (liquid B) Iron oxide precipitation solvent | | | | Formulation of the 3rd fluid (liquid C) — | | | |
|---|---|---|---|---|---|---|---|---|---|---|---|
| Formulation [wt %] | | | | Formulation [wt %] | | | | Formulation [wt %] | | | |
| Raw material [wt %] | Raw material [wt %] | pH | pH [° C.] | Raw material [wt %] | Raw material [wt %] | pH | pH [° C.] | Raw material [wt %] | Raw material [wt %] | Raw material [wt %] | pH | pH [° C.] |
| $Fe(NO_3)_3$ $9H_2O$ [2.00 wt %] | Pure water [98.00 wt %] | 1.8 | 26.6 | NaOH [9.00 wt %] | Pure water [91.00 wt %] | >14 | — | Pure water [93.64 wt %] | 97 wt % $H_2SO_4$ [3.86 wt %] | TEOS [2.50 wt %] | <1 | — |

TABLE 4

Example 4

| Introduction flow rate [ml/min] | | | Introduction temperature (liquid sending temperature) [° C.] | | | Introduction pressure (liquid sending pressure) [MPaG] | | | Discharged liquid | |
|---|---|---|---|---|---|---|---|---|---|---|
| Liquid A | Liquid B | Liquid C | Liquid A | Liquid B | Liquid C | Liquid A | Liquid B | Liquid C | pH | Temperature [° C.] |
| 900 | 100 | 150 | 140 | 80 | 60 | 0.432 | 0.55 | 5.00 | 12.29 | 34.6 |

| Coating thickness [nm] | Shell/Core $SiO_2/Fe_2O_3$ Molar ratio | | Particle diameter (D) [nm] | Core particle diameter (Dc) [nm] | D/Dc |
|---|---|---|---|---|---|
| | Calcurated value | EDS | | | |
| — | 0.81 | 0.84 | 15.46 | 9.46 | 162.9% |

Figure 7:
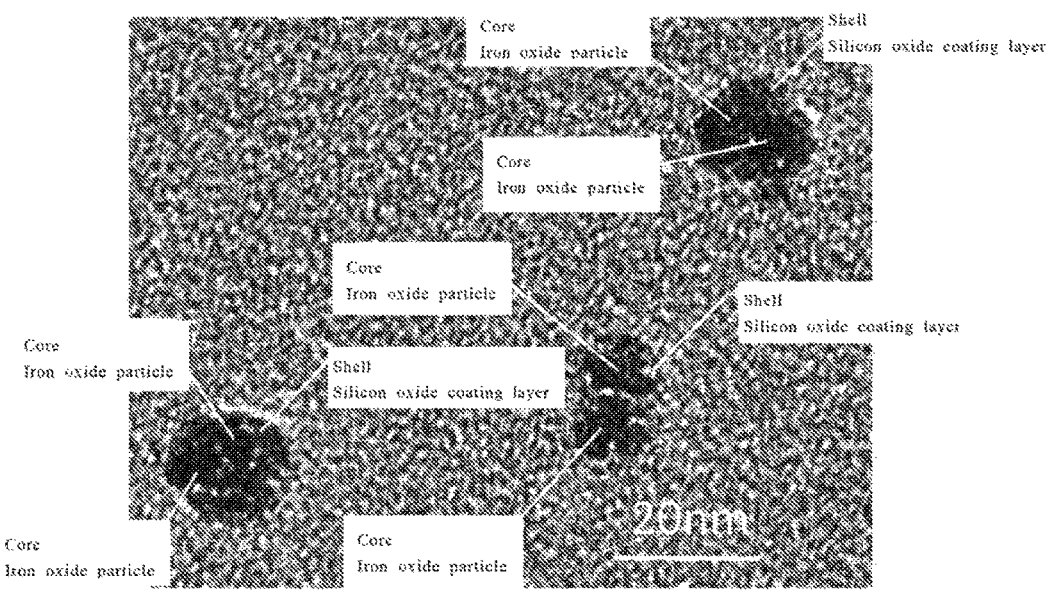
FIG. 7 shows a TEM photograph of the silicon oxide-coated iron oxide particles obtained in Example 4 of the present invention.

Then, the prepared iron oxide raw material liquid, the iron oxide precipitation solvent, and the silicon oxide raw material liquid were mixed in the same fluid processing apparatus as in Example 1. Table 4 shows the operating conditions of the fluid processing apparatus. The methods of washing, analysis and evaluation of particles are the same as in Example 1 except for evaluation of particle diameter (D) and core conversion particle diameter (Dc). The particle diameters (D) of Example 4 and Comparative Example 2 were calculated from the maximum distance between two points on the outer periphery of the silicon oxide-coated iron oxide particles, and the average value of the measured particle diameters of 100 particles was shown. Also the core particle diameter (Dc) of Example 4 and Comparative Example 2 were the maximum distance between two points on the outer periphery of the core iron oxide particles in the silicon oxide-coated iron oxide particles, and the average value of the measured core particle diameters of 100 particles was shown. A TEM photograph of the silicon oxide-coated iron oxide particles obtained in Example 4 is shown in FIG. 7. The core is an aggregate of a plurality of primary iron oxide particles, and the silicon oxide-coated iron oxide particles wherein the aggregates are coated with silicon oxide, was observed. The coating layer (shell) of the silicon oxide on particle diameter of the aggregate of the silicon oxide-coated iron oxide particles obtained in Example 4 was 50 nm or less. Not shown details of the particle diameter D or the core particle diameter Dc in FIG. 7, but D/Dc was about 162.9%. In the XRD measurement results, peaks of $\alpha\text{-}Fe_2O_3$ (hematite) were detected as in Example 1, and the FT-IR measurement results were similar to those in Example 1.

In the XRD measurement results, peaks of $\alpha\text{-}Fe_2O_3$ (hematite) were clearly detected in all conditions in Examples 1 to 4 and Comparative Example 1. As described above, in Examples 1 to 4, peaks of silicon oxide coating on the surface of the particles were not detected, and thus, the silicon oxide is considered to be amorphous.

Comparative Example 2

The iron oxide raw material liquid, the iron oxide precipitation solvent, and the silicon oxide raw material liquid were prepared using the high-speed rotary dispersion emulsification apparatus CLEAMIX (product name: CLM-2.2 S, M. Technique Co., Ltd.). Specifically, based on the formulation of the iron oxide raw material liquid shown in Comparative Example 2 of Table 5, the components of the iron oxide raw material liquid were mixed homogeneously by stirring using CLEARMIX at preparation temperature of 40° C. and at the rotor rotational speed of 20000 rpm for 30 min to prepare the iron oxide raw material liquid. Based on the formulation of the iron oxide precipitation solvent shown in Comparative Example 2 of Table 5, the components of the iron oxide precipitation solvent were mixed homogeneously by stirring using CLEARMIX at preparation temperature of 45° C. and at the rotor rotational speed of 15000 rpm for 30 min to prepare iron oxide precipitation solvent. Furthermore, based on the formulation of the silicon oxide raw material liquid shown in Comparative Example 2 of Table 5, the components of the silicon oxide raw material liquid were mixed homogeneously by stirring using CLEARMIX at preparation temperature of 20° C. and at the rotor rotational speed of 6000 rpm for 10 min to prepare the silicon oxide raw material liquid.

Figure 6:
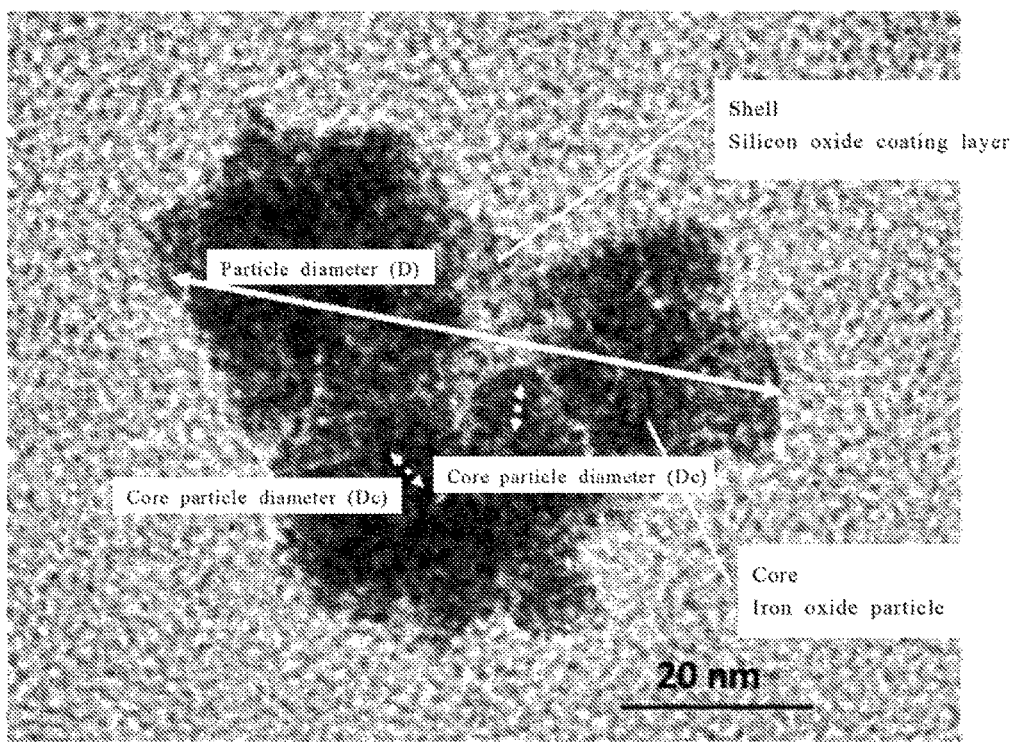
FIG. 6 shows a TEM photograph of the silicon oxide-coated iron oxide particles obtained in Comparative Example 2 of the present invention.

Regarding the substances represented by the chemical formula and abbreviations set forth in Table 5, 60 wt % $HNO_3$ is concentrated nitric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3 \cdot 9H_2O$ is iron nitrate nonahydrate (Kanto Chemical Co., Inc.).

parative Example 2. As shown in FIG. 6, it is observed that the aggregate of primary particles of iron oxide as a core is coated with silicon oxide as a shell. The particles wherein the primary particle diameter of the iron oxide as a core cannot be recognized are also observed. Further, the particle diameter of the iron oxide aggregates in the silicon oxide-coated iron oxide particles obtained in Comparative Example 2, exceeds 50 nm. In the XRD measurement results, peaks of $\alpha$-$Fe_2O_3$ (hematite) were detected as in Example 1, and the FT-IR measurement results were similar to those in Example 1.

Comparative Example 3

Figure 9:
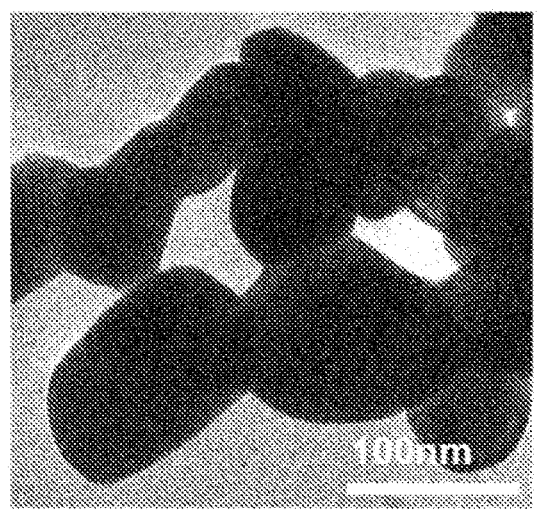
FIG. 9 shows a TEM photograph of the iron oxide particles of Comparative Example 3 of the present invention.

In Comparative Example 3, TEM observation, haze value, transmission spectrum, reflection spectrum and XRD of iron(III) oxide ($\alpha$-$Fe_2O_3$) produced by Wako Pure Chemical Industries, Ltd. were measured in the same manner as in Example 1. FIG. 9 shows a TEM photograph of the iron oxide particles of Comparative Example 3. The average primary particle diameter was 119.6 nm. In the production of a TEM observation sample of Comparative Example 3, the above commercially available iron(III) oxide ($\alpha$-$Fe_2O_3$)

TABLE 5

| Comparative Example 2 | | | | | | | | | | |
|---|---|---|---|---|---|---|---|---|---|---|
| Formulation of the 1st fluid (liquid A) Iron oxide raw material liquid | | | Formulation of the 2nd fluid (liquid B) Iron oxide precipitation solvent | | | Formulation of the 3rd fluid (liquid C) — | | | | |
| Formulation [wt %] | | | Formulation [wt %] | | | Formulation [wt %] | | | | |
| Raw material [wt %] | Raw material [wt %] | pH [° C.] | Raw material [wt %] | Raw material [wt %] | pH [° C.] | Raw material [wt %] | Raw material [wt %] | Raw material [wt %] | pH | pH [° C.] |
| $Fe(NO_3)_3$ $9H_2O$ [2.00 wt %] | Pure water [98.00 wt %] | 1.8  26.6 | NaOH [9.00 wt %] | Pure water [91.00 wt %] | >14  — | Pure water [97.52 wt %] | 60 wt % $HNO_3$ [2.11 wt %] | TEOS [0.37 wt %] | <1 | — |

TABLE 6

| Comparative Example 2 | | | | | | | | | | |
|---|---|---|---|---|---|---|---|---|---|---|
| Introduction flow rate [ml/min] | | | Introduction temperature (liquid sending temperature) [° C.] | | | Introduction pressure (liquid sending pressure) [MPaG] | | | Discharged liquid | |
| Liquid A | Liquid B | Liquid C | Liquid A | Liquid B | Liquid C | Liquid A | Liquid B | Liquid C | pH | Temperature [° C.] |
| 400 | 50 | 50 | 143 | 83 | 25 | 0.329 | 0.50 | 0.50 | 12.99 | 23.4 |

Then, the prepared iron oxide raw material liquid, the iron oxide precipitation solvent, and the silicon oxide raw material liquid were mixed in the same fluid processing apparatus as in Example 1. Table 6 shows the operating conditions of the fluid processing apparatus. The methods of washing, analysis and evaluation of particles are the same as in Example 4. As a result of TEM observation of the silicon oxide-coated iron oxide particles obtained in Comparative Example 2, iron oxide particles wherein the entire surface of one iron oxide particle is uniformly coated with silicon oxide, were not observed, and many particles wherein a plurality of iron oxide particles is coated with silicon oxide were observed. FIG. 6 shows a TEM photograph of the silicon oxide-coated iron oxide particles obtained in Comwas used without washing. In the XRD measurement results, peaks of $\alpha$-$Fe_2O_3$ (hematite) were clearly detected.

FIG. 5 shows the reflection spectrum at the wavelength from 380 nm to 780 nm using the respective powders of the silicon oxide-coated iron oxide particles obtained in Example 1, 2 and 4, the iron oxide particles obtained in Comparative Example 1, the silicon oxide-coated iron oxide particles obtained in Comparative Example 2, and the iron oxide particles of Comparative Example 3. The average reflectivities of the silicon oxide-coated iron oxide particles or iron oxide particles obtained in Examples 1 to 4 and Comparative Examples 1 to 3 for the light of the wavelengths from 620 nm to 750 nm were calculated from each reflectivity, and are shown in Table 7.

TABLE 7

| | Average reflectivity for the light of the wavelengths of 620 to 750 nm (%) |
|---|---|
| Example 1 | 18.1 |
| Example 2 | 23.7 |
| Example 3 | 20.2 |
| Example 4 | 19.2 |
| Comparative Example 1 | 27.9 |
| Comparative Example 2 | 27.8 |
| Comparative Example 3 | 29.3 |

As shown in Table 7, while the average reflectivity of the silicon oxide-coated iron oxide particles obtained in Examples 1 to 4 in the region of wavelengths of 620 to 750 nm was 25% or less, those of the iron oxide particles obtained in Comparative Examples 1 to 3 exceeded 25%. This result is caused by a change in color characteristics by amorphous silicon oxide coating.

Further, the reflectivity of the silicon oxide-coated iron oxide particles obtained in Example 1 for the light of the wavelength of around 550 to 780 nm, is low as compared with that of the iron oxide particles obtained in Comparative Example 1. This shows the result that amorphous silicon oxide coating gives a change in color characteristics. Further, the reflectivity of the silicon oxide-coated iron oxide particles obtained in Example 2 for the light of the wavelength of around 550 to 780 nm, is higher than that of the silicon oxide-coated iron oxide particles obtained in Example 1. This shows that the color characteristics change by addition of an acetyl group to the silicon oxide-coated iron oxide particles. This result indicates that the color characteristics change by changing a functional group contained in the particles. Also, the reflectivity of the silicon oxide-coated iron oxide particles obtained in Example 3 for the light of the wavelength of around 550 to 780 nm, is lower than that of the silicon oxide-coated iron oxide particles obtained in Example 2, and is higher than that of the silicon oxide-coated iron oxide particles obtained in Example 1 (not shown in FIG). However, significant difference in reflectivity was not observed between the iron oxide particles of Comparative Example 1 without silicon oxide coating on their surface and the iron oxide aggregates coated with silicon oxide of Comparative Example 2 (the silicon oxide-coated iron oxide wherein the particle diameter of the iron oxide particle aggregate exceeds 50 nm). Further, the reflectivity for the light of the wavelength of 550 to 780 nm of the silicon oxide-coated iron oxide particles obtained in Example 4 wherein an aggregate of iron oxide particles is coated with silicon oxide (the silicon oxide-coated iron oxide wherein the particle diameter of the iron oxide particle aggregate is 50 nm or less), is slightly higher than that of Example 1, and is lower than that of the silicon oxide-coated iron oxide particles as in Comparative Example 2 wherein an aggregate of iron oxide particles is coated with silicon oxide, and the particle diameter of the aggregate of iron oxide particles exceeds 50 nm. It was found that reflectivity could be controlled by a coating condition of the surface of iron oxide particles with silicon oxide. On the other hand, it was found that the effect on color characteristics was lowered when aggregates of iron oxide particles, particularly aggregates of iron oxide particles having more than 50 nm diameter were coated with silicon oxide.

Figure 8:
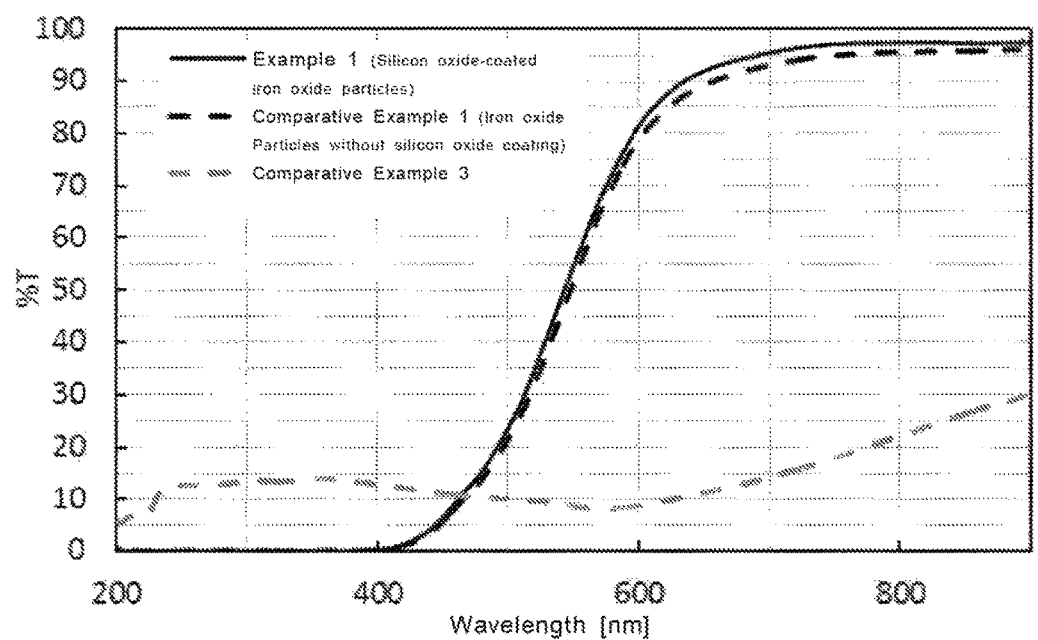
FIG. 8 shows the transmission spectrum of the dispersions in propylene glycol of the silicon oxide-coated iron oxide particles obtained in Example 1, the iron oxide particles obtained in Comparative Example 1, and the iron oxide particles of Comparative Example 3 respectively.

FIG. 8 shows the transmission spectrum measurement result of the dispersion wherein the silicon oxide-coated iron oxide particles obtained in Example 1 were dispersed in propylene glycol, and the dispersions wherein the iron oxide particles of Comparative Examples 1 and 3 were dispersed in propylene glycol. The silicon oxide-coated iron oxide particle dispersion obtained in Example 1 did not substantially transmit the ultraviolet light of the wavelength of 200 to 400 nm, and the transmittance at the wavelength of 420 nm was 1.64%. Further, the iron oxide particle dispersion obtained in Comparative Example 1 did not substantially transmit the ultraviolet light of the wavelength of 200 to 400 nm, and the transmittance at the wavelength of 420 nm was 1.73%. The transmittance of the dispersions of Example 1 and Comparative Example 1 at the wavelength of 620 to 780 nm was found to be more than 80%. In other words, it was found that the dispersions absorbed a light of the wavelength of 200 to 420 nm, and transmitted other lights, particularly a light of the wavelength of 620 to 780 nm. In contrast, the transmittance of the iron oxide particle dispersion of Comparative Example 3 in the region of the wavelength of 200 to 420 nm, was around 10%, and the transmittance in the wavelength of 620 to 780 nm was 20% at maximum. Therefore, clear difference between the absorption region and the transmission region was not observed. Although not shown in FIG. 8, the silicon oxide-coated iron oxide particle dispersion obtained in Example 4 did not substantially transmit the ultraviolet light of the wavelength of 200 to 400 nm, and the transmittance at the wavelength of 420 nm was 1.89%, and the transmittance at the wavelength of 620 to 780 nm was found to be more than 80%, though it was slightly inferior to the properties of the particles obtained in Example 1.

Incidentally, the transmission spectrum of the dispersion wherein the silicon oxide-coated iron oxide particles obtained in Example 2 were dispersed in butyl acetate at the iron oxide ($Fe_2O_3$) concentration of 0.05 wt %, was measured, and was almost similar to those of the above dispersions of Example 1 and Comparative Example 1.

The haze value of the dispersion wherein the silicon oxide-coated iron oxide particles obtained in above Example 1 was dispersed in propylene glycol at a $Fe_2O_3$ concentration of 0.05 wt % was 0.00%, and the haze value of the dispersion wherein the particles obtained in Example 1 was dispersed in water at a $Fe_2O_3$ concentration of 0.31 wt % was 0.08(0.00)%. Accordingly both dispersions were highly transparent dispersions. Further, the haze value of the dispersion wherein the silicon oxide-coated iron oxide particles obtained in Example 1 was dispersed in water at a $Fe_2O_3$ concentration of 2.0 wt % was 0.89%, and thus, it was a highly transparent dispersion. The haze value of the dispersion wherein the iron oxide particles of Comparative Example 3 was dispersed in propylene glycol at a $Fe_2O_3$ concentration of 0.02 wt % was 21.9%, and the haze value of the dispersion wherein the iron oxide particles of Comparative Example 3 was dispersed in water at a $Fe_2O_3$ concentration of 0.31 wt % was 15.9%. Further, the haze value of the dispersion wherein the iron oxide particles of Comparative Example 3 was dispersed in water at a $Fe_2O_3$ concentration of 2.0 wt % was 23.4%, and obvious turbidity was observed. The haze value of the dispersion wherein the iron oxide particles obtained in Comparative Example 1 was dispersed in water at a $Fe_2O_3$ concentration of 2.0 wt % was 2.56%, and turbidity was observed.

The haze value of the dispersion wherein the silicon oxide-coated iron oxide particles obtained in above Example 2 was dispersed in butyl acetate at a $Fe_2O_3$ concentration of 0.05 wt % was 0.12%, and the haze value of the dispersion wherein the particles obtained in Example 2 was dispersed in butyl acetate at a $Fe_2O_3$ concentration of 0.31 wt % was 0.22%, and both were highly transparent dispersions. Further, the haze value of the dispersion wherein the particles obtained in Example 2 was dispersed in butyl acetate at a $Fe_2O_3$ concentration of 2.0 wt % was 1.26%, and it was a transparent dispersion.

The haze value of the dispersion wherein the silicon oxide-coated iron oxide particles obtained in above Example 3 was dispersed in propylene glycol at a $Fe_2O_3$ concentration of 0.05 wt % was 0.09%, and the haze value of the dispersion wherein the particles obtained in Example 3 was dispersed in water at a $Fe_2O_3$ concentration of 0.31 wt % was 0.14%, and both were highly transparent dispersions. Further, the haze value of the dispersion wherein the particles obtained in Example 3 was dispersed in water at a $Fe_2O_3$ concentration of 2.0 wt % was 0.54%, and it was a highly transparent dispersion.

The haze value of the dispersion wherein the silicon oxide-coated iron oxide particles obtained in above Example 4 was dispersed in propylene glycol at a $Fe_2O_3$ concentration of 0.05 wt % was 0.91%, and the haze value of the dispersion wherein the particles obtained in Example 4 was dispersed in water at a $Fe_2O_3$ concentration of 0.31 wt % was 1.46%, and it was a highly transparent dispersion, though it is not to the extent of a silicon oxide-coated iron oxide particles obtained in Example 1. Further, the haze value of the dispersion wherein the particles obtained in Example 4 is dispersed in water at a $Fe_2O_3$ concentration of 2.0 wt % is 1.64%, and it was a highly transparent dispersion, though it is not to the extent of a silicon oxide-coated iron oxide particles obtained in Example 1.

From the above, when the silicon oxide-coated iron oxide particles obtained in Examples 1 to 4 or a composition thereof is used in a paint, coloring of the paint itself, color characteristics and designability of a product are not impaired, and they can be suitably used. On the other hand, regarding the iron oxide particles of Comparative Example 3, difference between transmission region and absorption region in the ultraviolet-visible region is not clearly observed, and the particles have strong reflection property in red color region, and thus coloring of the paint itself, color characteristics and designability of a product are impaired. Further, regarding the iron oxide particles obtained in Comparative Example 1 and the silicon oxide-coated iron oxide particles obtained in Comparative Example 2, the average reflectivity in the range of the wavelength of 620 to 750 nm is more than 25%, and the powers of the iron oxide particles obtained in Comparative Example 1 look yellowish as compared with the silicon oxide-coated iron oxide particles obtained in Example 1. Thus, coloring of the paint itself, color characteristics and designability of a product are impaired. Further, the silicon oxide-coated iron oxide particles obtained in Examples 1 and 2 can express a deep red color, because the reflectivity of the silicon oxide-coated iron oxide particles for the light of the wavelength of around 550 to 780 nm is reduced as compared with that of the iron oxide particles obtained in Comparative Example 1. The silicon oxide-coated iron oxide particles as obtained in Example 1 can express a much deeper red color, when the reflectivity for the light of the wavelength of around 550 to 780 nm is lower than that of the silicon oxide-coated iron oxide particles obtained in Example 2. Thus, it is possible to use properly silicon oxide-coated iron oxide particles depending on a desired color and designability.

The invention claimed is:

1. A composition for a red-colored laminated coating film, comprising silicon oxide-coated iron oxide particles, wherein at least a part of the surface of said iron oxide particles is coated with silicon oxide,
   wherein the iron oxide particles comprised in the composition for a red-colored laminated coating film consist essentially of $\alpha\text{-}Fe_2O_3$,
   wherein said silicon oxide comprises amorphous silicon oxide,
   wherein the diameter of said iron oxide particles is 1 to 50 nm, and
   wherein the average reflectivity of said silicon oxide-coated iron oxide particles for the light of the wavelengths of 620 to 750 nm is 25% or less.

2. The composition for a red-colored laminated coating film according to claim 1, wherein the transmittance of a dispersion comprising said silicon oxide-coated iron oxide particles for the light of the wavelength of 200 to 420 nm is 2.0% or less, and the transmittance of the same for the light of the wavelength of 620 to 780 nm is 80% or more.

3. The composition for a red-colored laminated coating film according to claim 1, wherein the haze value of said silicon oxide-coated iron oxide dispersion is 2.0% or less at an iron oxide concentration of 2 wt % in a dispersion comprising said silicon oxide-coated iron oxide particles.

4. The composition for a red-colored laminated coating film according to claim 1, wherein said silicon oxide-coated iron oxide particles are the particles wherein at least a part of the surface of an iron oxide particle is coated with silicon oxide, and
   wherein the primary particle diameter of said iron oxide particle is 1 to 50 nm, and the primary particle diameter of said silicon oxide-coated iron oxide particles is 100.5% or more and 190% or less relative to said primary particle diameter of the iron oxide particle.

5. The composition for a red-colored laminated coating film according to claim 4, wherein said silicon oxide-coated iron oxide particles are core-shell silicon oxide-coated iron oxide particles wherein the entire surface of one core iron oxide particle is coated with the shell silicon oxide.

6. The composition for a red-colored laminated coating film according to claim 1, wherein said silicon oxide-coated iron oxide particles are the particles wherein at least a part of the surface of aggregates of a plurality of iron oxide particles is coated with silicon oxide, and
   wherein the diameter of said aggregates is 1 to 50 nm, and the diameter of said silicon oxide-coated iron oxide particles is 100.5% or more and 190% or less relative to the diameter of said aggregates.

7. The composition for a red-colored laminated coating film according to claim 1, comprising a perylene pigment.

8. A paint comprising the composition for a red-colored laminated coating film according to claim 1.

9. A coating film comprising the composition for a red-colored laminated coating film according to claim 1.

10. A vehicle equipped with the coating film according to claim 9.

* * * * *